US010751318B2

(12) United States Patent
Liu

(10) Patent No.: US 10,751,318 B2
(45) Date of Patent: Aug. 25, 2020

(54) PHARMACEUTICAL CO-CRYSTAL AND USE THEREOF

(71) Applicant: SYN-NAT PRODUCTS ENTERPRISE LLC, Edison, NJ (US)

(72) Inventor: Xiaozhong Liu, Potomac, MD (US)

(73) Assignee: SYN-NAT PRODUCTS ENTERPRISE LLC, Potomac, MD (US)

(*) Notice: Subject to any disclaimer, the term of this patent is extended or adjusted under 35 U.S.C. 154(b) by 166 days.

(21) Appl. No.: 15/574,015

(22) PCT Filed: May 17, 2016

(86) PCT No.: PCT/US2016/032856
§ 371 (c)(1),
(2) Date: Nov. 14, 2017

(87) PCT Pub. No.: WO2016/187191
PCT Pub. Date: Nov. 24, 2016

(65) Prior Publication Data
US 2018/0289662 A1    Oct. 11, 2018

Related U.S. Application Data

(60) Provisional application No. 62/163,256, filed on May 18, 2015.

(51) Int. Cl.
*A61K 31/282* (2006.01)
*A61K 31/192* (2006.01)
(Continued)

(52) U.S. Cl.
CPC ............ *A61K 31/282* (2013.01); *A61K 31/12* (2013.01); *A61K 31/122* (2013.01);
(Continued)

(58) Field of Classification Search
CPC .. A61K 33/243; A61K 31/282; A61K 31/205; A61K 31/192; A61P 31/12; A61P 35/00
See application file for complete search history.

(56) References Cited

U.S. PATENT DOCUMENTS 3,290,365 A * 12/1966 Greene ................ C08G 63/137
528/307
5,455,270 A * 10/1995 Kaplan ................ A61K 9/0019
514/492

(Continued)

FOREIGN PATENT DOCUMENTS

WO    WO 2011/029415 A1    3/2011
WO    WO 2015/058067 A1    4/2015
(Continued)

OTHER PUBLICATIONS

Korotkova et al. (Procedia Chemistry, 10, 473-476, 2014) (Year: 2014).*

(Continued)

*Primary Examiner* — Theodore R. West
(74) *Attorney, Agent, or Firm* — Nixon & Vanderhye P.C.

(57) ABSTRACT

The current invention relates to a co-crystal of carboplatin with 1,2-cis-cyclobutane dicarboxylate and its pharmaceutical use. The co-crystal of the current invention can be used in the treatment and/or prevention of cancer, as well as the treatment and/or prevention of a virus infection.

17 Claims, 13 Drawing Sheets

(51) Int. Cl.

| | | |
|---|---|---|
| *A61K 31/205* | (2006.01) | |
| *A61K 45/06* | (2006.01) | |
| *C07F 15/00* | (2006.01) | |
| *A61K 31/12* | (2006.01) | |
| *A61K 31/69* | (2006.01) | |
| *A61K 31/519* | (2006.01) | |
| *A61K 38/06* | (2006.01) | |
| *A61K 31/122* | (2006.01) | |
| *A61K 31/575* | (2006.01) | |
| *A61K 36/886* | (2006.01) | |
| *A61K 31/513* | (2006.01) | |
| *A61P 31/12* | (2006.01) | |
| *A61P 31/20* | (2006.01) | |
| *A61P 31/14* | (2006.01) | |
| *A61P 35/00* | (2006.01) | |

(52) U.S. Cl.
CPC .......... *A61K 31/513* (2013.01); *A61K 31/519* (2013.01); *A61K 31/575* (2013.01); *A61K 31/69* (2013.01); *A61K 36/886* (2013.01); *A61K 38/063* (2013.01); *A61K 45/06* (2013.01); *A61P 31/12* (2018.01); *A61P 31/14* (2018.01); *A61P 31/20* (2018.01); *A61P 35/00* (2018.01); *C07F 15/00* (2013.01); *C07F 15/0093* (2013.01); *C07B 2200/13* (2013.01); *Y02A 50/385* (2018.01); *Y02A 50/387* (2018.01); *Y02A 50/393* (2018.01); *Y02A 50/395* (2018.01); *Y02A 50/463* (2018.01)

(56) References Cited

U.S. PATENT DOCUMENTS

| | | | |
|---|---|---|---|
| 6,340,770 | B1 | 1/2002 | Kwon et al. |
| 6,699,901 | B1 | 3/2004 | Yang et al. |
| 7,927,613 | B2 | 4/2011 | Almarsson et al. |
| 2003/0103896 | A1 | 6/2003 | Smith |
| 2005/0165093 | A1 | 7/2005 | Wang et al. |
| 2007/0197517 | A1 | 8/2007 | Jani et al. |
| 2008/0063642 | A1 | 3/2008 | Adelman et al. |
| 2008/0161251 | A1 | 7/2008 | Curry et al. |
| 2009/0281319 | A1 | 11/2009 | Du Preez |
| 2010/0068178 | A1 | 3/2010 | Gokaraju et al. |
| 2011/0287110 | A1 | 11/2011 | Dewhirst et al. |

FOREIGN PATENT DOCUMENTS

| | | | |
|---|---|---|---|
| WO | WO 2016/172393 | A1 | 10/2016 |
| WO | WO 2016/187191 | A1 | 11/2016 |
| WO | WO 2016/205782 | A1 | 12/2016 |
| WO | WO 2016/205785 | A1 | 12/2016 |
| WO | WO 2016/210418 | A1 | 12/2016 |

OTHER PUBLICATIONS

Li, GQ et al., "Effect of Dicyclopatin, a Novel Platinum Chemotherapeutical Drug, on Inhibiting Cell Growth and Inducing Cell Apoptosis," PLOS One, 7(11):e48394 (2012).

Omar, E.K. et al,, "Does the Key to Treat Rheumatoid Nodules Lie with Oncology?—Is Cisplatin an Option?," BioMed Central Musculoskeletal Disorders, 14 (Suppl. 1): A5, BioMed Central (2013).

Kreiner, B. et al,, "Neuroendocrine Carcinoma of the Seminal Vesicles Presenting with Lambert Eaton Syndrome: a Case Report," Journal of Medical Case Reports, 4:320, p. 1-4, BioMed Central (2010).

Li, S. et al., "Phase I Clinical Trial of the Novel Platin Complex Dicycloplatin: Clinical and Pharmacokinetic Results," Int'l Journal of Clinical Pharmacology and Therapeutics, vol. 51, No. 2, pp. 96-105 (2013).

Liu, KJ et al., "A Double-Blind, Randomized Phase II Study of Dicycloplatin Plus Paclitaxel Versus Carboplatin Plus Paclitaxel as First-Line Therapy for Patients with Advanced Non-Small-Cell Lung Cancers," Arch Med Sci, 10, 4: 717-724, Elsevier, Netherlands (2014).

Yang, X. et al., "Determination Methods for the Anticancer Drug Dicycloplatin, a Supramolecule Assembled Through Hydrogen Bonding", Analyst, 140:2704-2712, The Royal Society of Chemistry (2015).

International Search Report of PCT/US2016/028720 dated Jul. 15, 2016, issued by the International Bureau.

International Search Report of PCT/US2016/032856 dated Aug. 16, 2016, issued by the International Bureau.

International Search Report of PCT/US2016/038333 dated Sep. 28, 2016, issued by the International Bureau.

International Search Report of PCT/US2016/038340 dated Sep. 13, 2016, issued by the International Bureau.

International Search Report of PCT/US2016/039572 dated Sep. 23, 2016, issued by the International Bureau.

Hill, W.E., et al., "Synthesis, Characterization and Anti-Tumor Testing of Some Platinum (II) AMINE Complexes Containing 1,1- and 1,2-Cyclobutanedicarboxylate Ligands," Chem. Biol. Interactions, 73 (1990) 337-351.

\* cited by examiner

| D-H⋯A | d(D⋯A)/Å | D-H⋯A | d(D⋯A)/Å |
|---|---|---|---|
| N(1)-H(1A)⋯O(5') | 2.86(6) | N(2)-H(2B)⋯O(5) | 3.16(12) |
| N(1)-H(1B)⋯O(4) | 3.13(5) | O(5)-H(5)⋯O(3) | 3.07(12) |
| N(1)-H(1B)⋯O(7) | 3.17(8) | O(7)-H(7A)⋯O(2) | 3.09(6) |
| N(2)-H(2B)⋯O(1) | 3.20(4) | O(7)-H(7A)⋯N(1) | 3.17(8) |

| HV | WD | mag | mode | HFW | dwell | det | ——50 μm—— |
|---|---|---|---|---|---|---|---|
| 10.0kV | 5.3mm | 1,000x | SE | 240μm | 6μs | TLD | Nova Nano SEM230 |

| HV | WD | mag | mode | HFW | dwell | det | 5 μm |
|---|---|---|---|---|---|---|---|
| 10.0kV | 5.2mm | 10,000x | SE | 24.0μm | 6μs | TLD | Nova Nano SEM230 |

| HV | WD | mag | mode | HFW | dwell | det | ———3 μm——— |
|---|---|---|---|---|---|---|---|
| 10.0kV | 5.2mm | 20,000x | SE | 12.0μm | 6μs | TLD | Nova Nano SEM230 |

PHARMACEUTICAL CO-CRYSTAL AND USE THEREOF

FIELD OF THE INVENTION

The current invention relates to co-crystals of carboplatin with 1,2-cis-cyclobutane dicarboxylate and its pharmaceutical use. The co-crystals of the current invention may be used in the treatment and/or prevention of diseases such as cancer and viral infections.

BACKGROUND OF THE INVENTION

Cisplatins have been used widely in clinical medicine as an antitumor drug since its antitumor effect was discovered for cis-dichlorodiaminoplatin. Rosenberg et al. *Nature*, 1965, 205: 698; *Nature*, 1972, 222: 385. Although cisplatins exhibit therapeutic effects in cancers such as genitourinary cancer, nasopharyngeal cancer, cephalocircular cancer and lung cancer, these drugs also lead to severe side effects. The undesirable effects, such as nephrotoxicity, neurotoxicity, ototoxicity, nausea, and vomiting, put considerable constraints to dosage and long term use of cisplatins.

Carboplatin, one of the second-generation antitumor drugs of platin analogues, has received worldwide approval and use due to its lower toxicity in comparison to cisplatin. Unfortunately, carboplatin still results in a number of side effects, such as myelosuppression. In addition, carboplatin may be used only for a limited spectrum of cancers. Therefore, the search continues for orally active carboplatin analog compounds that are less toxic, cause less drug-resistance and provide more versatility.

Pharmaceutical co-crystallization has attracted great amount of academic, industrial and therapeutic interests by co-crystallization of two or more pure compounds with crystal engineering to create a new functional material. Specifically, pharmaceutical co-crystals are defined as "co-crystals in which the target molecule or ion is an active pharmaceutical ingredient, API, and it bonds to the co-crystal former(s) through hydrogen bonds." Almarsson M. and Zaworotko J., *Chem. Commun.*, 2004: 1889. Pharmaceutical co-crystals are nonionic supramolecular complexes and can be used to improve physiochemical property issues such as solubility, stability and bioavailability in pharmaceutical development without changing the chemical composition of the API.

Consequently, it is desirable to improve the physiochemical and therapeutic properties of cisplatin, carboplatin and other platin with co-crystallization technology. In some cases, there is no need to change the basic structure of the platin API, while properties such as solubility, stability, permeability and bioavailability would be improved. For example, it would be possible to significantly enhance the bioavailabiltiy of a platin API with co-crystallization, so that the co-crystal can be therapeutically effective in certain environment of use and maintain the level for a prolonged period of time.

Through the screening of the co-crystal formers suitable for carboplatin, 1,2-cis-cyclobutane dicarboxylate was found as an appropriate co-crystal former in this invention, which effectively meet the envisioned objectives, such as increased solubility, stability and bioavailability and more versatility in pharmaceutical uses.

SUMMARY OF THE INVENTION

The present invention relates to a co-crystal of carboplatin and 1,2-cis-cyclobutane dicarboxylate (hereinafter the co-crystal may be referred to as CBCBP), and methods of making and using the same. In some embodiments, the co-crystal has a structure of formula (I).

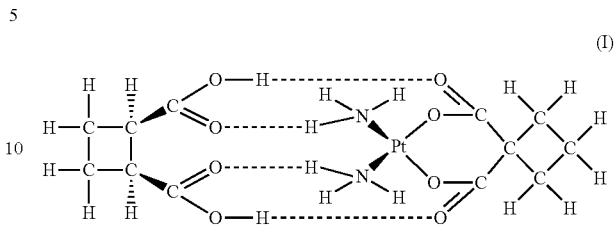

In some embodiments, CBCBP comprises (i) 1,2-cis-cyclobutane dicarboxylate as a co-former; and (ii) carboplatin as a co-former and the active pharmaceutical ingredient (API). CBCBP is formed where the API (carboplatin) and the co-crystal former 1,2-cis-cyclobutane dicarboxylate are bonded together through hydrogen bonds. Other non-covalent interactions may also be present.

In one aspect, the current invention provides carboplatin-based co-crystals that have a sufficient level of bioavailablity to be therapeutically effective in pharmaceutical use and in some embodiments the level can be maintained for a prolonged period of time.

In another aspect, the current invention relates to CBCBP for use in medicine, e.g. for prevention or treatment of diseases such as but not limited to cancers and viral infections. Some embodiments relate to use of CBCBP in manufacturing a medicament for prevention or treatment of cancers or viral infections in a subject, such as a human. Some embodiments relate to method of preventing or treating cancers and viral infections in a subject, such as a human, with a pharmaceutical composition comprising CBCBP. In some embodiments, the cancers are treated by contacting cancer cells with CBCBP. In some embodiments, the viral infection is treated by contacting the infected cells with CBCBP.

In one aspect, the current invention relates to a method to make the CBCBP co-crystal by milling or grinding carboplatin, 1,2-cis-cyclobutane dicarboxylate, and a small amount of solvent. In some embodiments, a process is provided to prepare the CBCBP, comprising: (i) providing carboplatin and 1,2-cis-cyclobutane dicarboxylate at proper ratios in an appropriate solvent; (ii) slurrying or stirring the mixtures for a period of time; and (iii) isolating the co-crystal formed thereby.

In another aspect, the present invention relates to a pharmaceutical composition comprising an effective amount of CBCBP and the uses of such composition to prevent or treat cancers and viral infections. In some embodiments, the pharmaceutical composition comprises CBCBP with no additional therapeutic agent or adjuvant. In some other embodiments, the pharmaceutical composition comprising CBCBP further comprises at least one additional therapeutic agent or adjuvant. For example, the therapeutic agent or adjuvant may include but are not limited to: folic acid, coenzyme Q10, curcumin, glutathione (GSH), aloe vera, oryzanol, 5-fluorouracil, bortezomib, and a combination thereof.

In yet another aspect, the amount of CBCBP in the pharmaceutical composition administered to a subject may be about 0.005 to 20 mg/kg body weight, about 0.005 to 10 mg/kg body weight, about 0.005 to 5 mg/kg body weight, about 0.005 to 2.5 mg/kg body weight, 0.01 to 20 mg/kg body weight, about 0.01 to 10 mg/kg body weight, about 0.01 to 5 mg/kg body weight, about 0.01 to 2.5 mg/kg body weight, 0.1 to 20 mg/kg body weight, about 0.1 to 10 mg/kg body weight, about 0.1 to 5 mg/kg body weight, or about 0.1 to 2.5 mg/kg body weight. The preferred amount of CBCBP depends on the particular disease to be treated and the subject's specific conditions.

In one aspect, the present invention relates to prevent or treat a disease in a subject in need thereof, comprising administering a pharmaceutical composition of the present invention to the subject. In particular, the disease may be a cancer or a viral infection.

In some embodiments, CBCBP may be used to prevent or treat cancer such as but not limited to: bladder cancer, non-small cell lung cancer, cervical cancer, anal cancer, pancreatic cancer, squamous cell carcinoma including head and neck cancer, renal cell carcinoma, skin cancer, melanoma, ovarian cancer, small cell lung cancer, endometrial cancer, glioblastoma, astroycytoma, oligodendroglioma, ependymoma, neurofibrosarcoma, meningioma, gastrointestinal stromal tumor, breast cancer, lung cancer, colorectal cancer, thyroid cancer, bone sarcoma, stomach cancer, oral cavity cancer, oropharyngeal cancer, gastric cancer, kidney cancer, liver cancer, prostate cancer, esophageal cancer, testicular cancer, gynecological cancer, colon cancer, brain cancer, leukemia, lymphoma, leucocythemia, and multiple myeloma. In particular, CBCBP may be used to prevent or treat prostate cancer, kidney cancer or leucocythemia.

In some embodiments, CBCBP may be used to prevent or treat viral infection by viruses such as but not limited to: adenovirus, herpes simplex virus, human pepillomavrus, VITAMIN K virus, smallpox virus, hepatitis B virus (HBV), and parvovirus B19, human astrovirus, norwalk virus, hepatitis A virus (HAV), severe acute respiratory syndrome virus, hepatitis C virus (HCV), yellow fever virus, dengue virus, West Nile virus, TBE virus, rubella virus, hepatitis E virus (HEV), human immunodeficiency virus (HIV), influenza virus, Lassa virus (LASV), Crimean-Congo hemorrhagic fever virus, Hantaan virus, Ebola virus, Marburg virus, Measles virus, mumps virus, parainfluenza virus, respiratory syncytial virus, rabies virus, and hepatitis D virus (HDV), rotavirus, orbivirus, coltivirus, Banna virus. In particular, CBCBP may be used to prevent or treat viral infections caused by HBV, HCV, HIV, or Hantaan virus. The effects of CBCBP on virus infection may be related to the ability of the platin complex to hamper the DNA or RNA replication process.

In another aspect, administration of the pharmaceutical composition according to the present invention can be via any common route as long as the target issue is available via the route. Suitable routes may include oral, buccal, by inhalation spray, sublingual, rectal, transdermal, vaginal, transmucosal, topical, nasal or intestinal administration; parenteral delivery, including intramuscular, subcutaneous, intramedullary injections, as well as intrathecal, direct intraventricular, orthotopic, intrademal, intraperitoneal, intravenous, intra-articular, intra-sternal, intra-synovial, intra-hepatic, intralesional, intracranial, intraperitoneal, intranasal, or intraocular injections or other modes of delivery. The preferred delivery route depends on the particular disease to be treated and the subject's specific conditions.

DETAILED DESCRIPTION OF THE INVENTION

Figure 1:
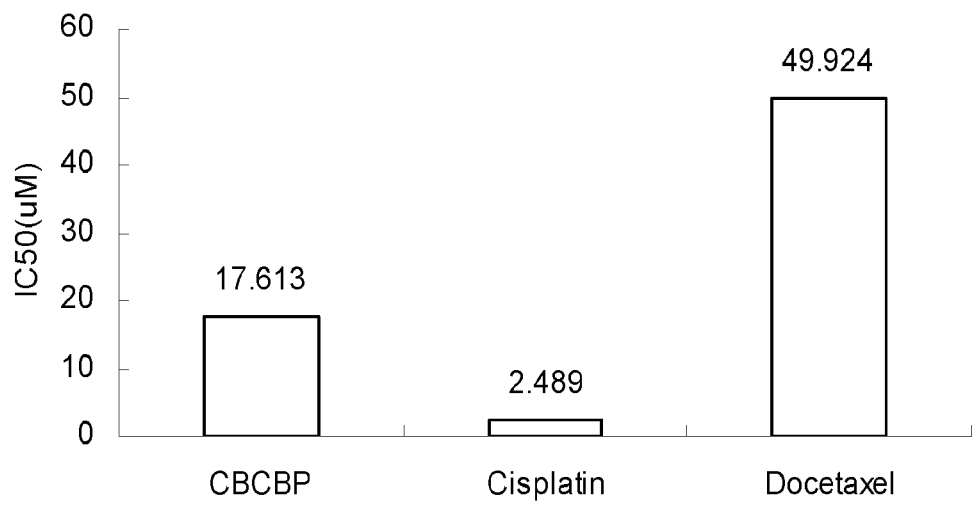
FIG. 1 shows the $IC_{50}$ of CBCBP and the control chemicals Docetaxel and cisplatin in PC-3 prostate cancer cell line.

The following description of certain embodiment(s) is merely exemplary in nature and is in no way intended to limit the invention, its application, or uses. As used throughout, ranges are used as shorthand for describing each and every value that is within the range. Any value within the range can be selected as the terminus of the range. In the event of a conflict in a definition in the present disclosure and that of a cited reference, the present disclosure controls. Unless defined otherwise, all technical and scientific terms used herein have the same meaning as is commonly understood by one of skill in the art to which this invention belongs. All patents and publications referred to herein are incorporated by reference in their entireties.

The term "effective amount" or "therapeutically effective amount" refers to that amount of a compound or combination of compounds as described herein that is sufficient to effect the intended application including, but not limited to, prophylaxis or treatment of diseases. A therapeutically effective amount may vary depending upon the intended application (in vitro or in vivo), or the subject and disease condition being treated (e.g., the weight, age and gender of the subject), the severity of the disease condition, the manner of administration, etc. which can readily be determined by one of ordinary skill in the art. The term also applies to a dose that will induce a particular response in target cells and/or tissues (e.g., the reduction of cell proliferation and/or morphological alteration of the tissue). The specific dose will vary depending on the particular compounds chosen, the dosing regimen to be followed, whether the compound is administered in combination with other compounds, timing of administration, the tissue to which it is administered, and the physical delivery system in which the compound is carried.

A therapeutic "effect" as that term is used herein, encompasses a therapeutic benefit and/or a prophylactic benefit. A prophylactic effect (e.g. terms such as "prophylaxis," "prevent" and "reducing the likelihood for developing") includes delaying or eliminating the appearance of a disease or condition, delaying or eliminating the onset of symptoms of a disease or condition, slowing, halting, or reversing the progression of a disease or condition, or any combination thereof by administering a drug before the onset of the disease or condition. A treatment effect (e.g. with terms such as "treatment" and "treat") includes reducing or eliminating the appearance of a disease or condition, reducing or eliminating the symptoms of a disease or condition, slowing, halting, or reversing the progression of a disease or condition, or any combination thereof by administering a drug after the onset of the disease or condition.

A "subject" as the term is used herein, refers to a human or non-human animal. In some embodiments, the subject is a mammal. In some embodiments, the subject is human.

When ranges are used herein to describe, for example, physical or chemical properties such as molecular weight or chemical formulae, all combinations and sub-combinations of ranges and specific embodiments therein are intended to be included. Use of the term "about" when referring to a number or a numerical range means that the number or numerical range referred to is an approximation within experimental variability (or within statistical experimental error), and thus the number or numerical range may vary. The variation is typically from 0% to 15%, including from 0% to 10%, including from 0% to 5% of the stated number or numerical range. The term "comprising" (and related terms such as "comprise" or "comprises" or "having" or "including") includes those embodiments such as, for example, an embodiment of any composition of matter, method or process that "consist of" or "consist essentially of" the described features.

Compounds used in the present invention also include crystalline and amorphous forms of those compounds, including, for example, polymorphs, pseudopolymorphs, solvates, hydrates, unsolvated polymorphs (including anhydrates), conformational polymorphs, and amorphous forms of the compounds, as well as mixtures thereof. "Crystalline form" and "polymorph" are intended to include all crystalline and amorphous forms of the compound, including, for example, polymorphs, pseudo-polymorphs, solvates, hydrates, unsolvated polymorphs (including anhydrates), conformational polymorphs, and amorphous forms, as well as mixtures thereof, unless a particular crystalline or amorphous form is referred to.

The present invention relates to a co-crystal comprising 1,2-cis-cyclobutane dicarboxylate and carboplatin. In some embodiments, the co-crystal of the present invention is designated as CBCBP and has the structure of formula (I):

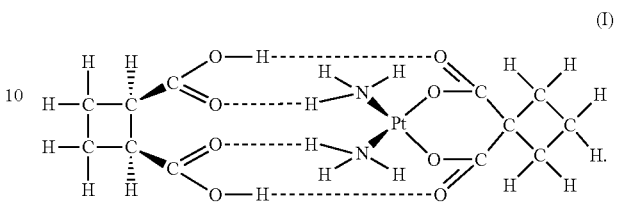

In some embodiments, the co-crystal of the present invention comprises: (i) 1,2-cis-cyclobutane dicarboxylate as a co-former; and (ii) carboplatin as a co-former and the active pharmaceutical ingredient (API). In one embodiment, carboplatin and 1,2-cis-cyclobutane dicarboxylate are bonded in 1:1 ratio.

As described here, the solid state of the co-crystal of the current invention is any crystalline polymorphic forms, or a mixture thereof. In some embodiments, the solid state of the co-crystal of the current invention is Form A, as shown in the X-ray powder diffraction pattern (XRPD) of FIG. 9. In some embodiments, the solid state of the co-crystal has a main peak between 5.5 and 7.5 in XRPD analysis, significantly different from the pattern of either 1,2-cis-cyclobutane dicarboxylate or carboplatin. Form A of the co-crystal of CBCBP in this invention was also confirmed by single crystal characterization and other determination methods. In one embodiment, the co-crystal of the current invention has properties and structure substantially similar to the data shown in Table 3. Amorphous forms of the co-crystal of the current invention and other forms may be obtained through different crystallization process.

The carboplatin-based co-crystal of the current invention (e.g. CBCBP) demonstrates a sufficient level of bioavailablity to be therapeutically effective in pharmaceutical use and maintains that level in a subject for a prolonged period of time.

CBCBP may be produced by a process comprising: (i) providing carboplatin and 1,2-cis-cyclobutane dicarboxylate at proper ratios in an appropriate solvent; (ii) slurrying or stirring the mixtures for a period of time; and (iii) isolating the co-crystal formed thereby. The specific conditions of the process may be adjusted to ensure optimized purity, quantity, and/or physiochemical properties. In some embodiments, the proper ratio is in the molar range of 1:0.1-1:20, 1:0.2-1:20, 1:0.3-1:20, 1:0.4-1:20, 1:0.5-1:20, 1:0.6-1:20, 1:0.7-1:20; 1:0.8-1:20, 1:0.9-1:20, 1:1-1:1.20, 1:2-1:20, 1:3-1:20, 1:4-1:20, 1:5-1:20, 1:6-1:18, 1:7-1:15, 1:8-1:13, 1:9-1:12, or 1:10-1:11. In one embodiment, the proper ratio is about 1:11 (molar). In some embodiments, the period of time for slurrying or stirring the mixtures may be in the range of 0.1-24 hours, 0.2-12 hours, 0.25-6 hours, 0.3-2 hours, 0.4-1 hour, or 0.5-1 hour. In one embodiment, the period of time for slurrying or stirring the mixtures may be about 0.5 hour. In some embodiments, the co-crystal compound may be obtained by drying, filtering, centrifugation, pipeting, or a combination thereof. In one embodiment, the co-crystal compound may be obtained by centrifugation.

The current invention relates to the pharmaceutical use of the co-crystal CBCBP, and methods of treating or preventing a disease in a subject in need thereof. In some embodiments, the method comprises administering to the subject a pharmaceutical composition comprising a therapeutically effective amount of CBCBP.

In some embodiments, the carboplatin-based co-crystal of the current invention (e.g. CBCBP) demonstrates advantageous therapeutic properties. For example, in some embodiments, CBCBP may be more effective in killing cancerous or virus-infected cells compared to carboplatin or other known drugs. In other embodiments, CBCBP may be less effective in killing cancerous or virus-infected cells compare to carboplatin or other known drugs or have substantially similar effects, but is less toxic to healthy and normal cells, resulting in a net health benefit. For instance, comparing to know platin analogues in the treatment of cancer cells or virus-infected cells, CBCBP is less toxic and much stable than cisplatin and carboplatin. In one embodiment, the advantageous effects of CBCBP may be reduced side effects. In some embodiments, CBCBP may demonstrate more versatility in pharmaceutical uses, e.g. when compared to carboplatin.

In some embodiments, the carboplatin-based co-crystal of the current invention (e.g. CBCBP) demonstrates advantageous physiochemical properties. For example, in some embodiments, CBCBP may have increased solubility, stability, and bioavailability. For example, in comparison with carboplatin, the CBCBP is much more stable and could be stable in solid form of various doses. Meanwhile, water solubility of CBCBP (~30 mg/mL) is much higher than carboplatin (18 mg/mL), providing significantly more possibility of formulations and administration.

In some embodiments, the $IC_{50}$ of CBCBP to reduce PC-3 cell number is about 17.613 μM; in another embodiment, the $IC_{50}$ of CBCBP to reduce LNCaP cell number is about 19.646 μM; in yet another embodiment, CBCBP shows minimum toxicity to HL-7002 cells, with much higher $IC_{50}$ (e.g. about 10 times) than cisplatin in similar conditions; and in yet another embodiment, CBCBP does not show toxicity to for HEK293 cells. In some embodiments, CBCBP demonstrates an $IC_{50}$ of about 17.613 μM to reduce PC-3 cell number, an $IC_{50}$ of about 19.646 μM to reduce LNCaP cell number, $IC_{50}$ of about 20.51 μM to reduce HL-7002 cell number, and no toxicity to HEK293 cells.

In some embodiments, the $IC_{50}$ of CBCBP to reduce A498 cell number is about 18.357 μM; in another embodiment, the $IC_{50}$ of CBCBP to reduce ACHN cell number is about 11.647 μM; in another embodiment, CBCBP shows only minimum toxicity to HL-7002 cells with an $IC_{50}$ of about 351 μM; and in yet another embodiment, CBCBP shows only minimum toxicity to HEK293 cells with an $IC_{50}$ of about 1204 μM. In one embodiment, CBCBP demonstrates an $IC_{50}$ of about 18.357 μM to reduce A498 cell number, an $IC_{50}$ of about 11.647 μM to reduce ACHN cell number, and only minimum toxicity to HL-7002 and HEK293 cells, with $IC_{50}$ of about 351 μM and 1204 μM, respectively.

In some embodiments, the $IC_{50}$ of CBCBP to inhibit Hantaan virus is about 33.684 ug/mL; in another embodiment, the $IC_{50}$ of CBCBP to inhibit secretion of surface antigen of the hepatitis B virus (HBsAg) is about 36.303 μg/ml; in yet another embodiment, the $IC_{50}$ of CBCBP to inhibit secretion of envelope antigen of hepatitis B viral protein (HBeAg) is about 67.311 μg/ml. In one embodiment, CBCBP demonstrates an $IC_{50}$ of about 33.684 ug/mL to inhibit Hantaan virus, an $IC_{50}$ of about 36.303 μg/mL to inhibit secretion of HBsAg, and is an $IC_{50}$ of about 67.311 μg/ml to inhibit secretion of HBeAg.

In some embodiments, the pharmaceutical composition may consist of CBCBP. In some embodiments, the pharmaceutical composition may comprise CBCBP and at least one additional therapeutic agent or adjuvant. The additional therapeutic agent or adjuvant may be selected from but is not limited to: folic acid, coenzyme Q10, curcumin, glutathione (GSH), aloe vera, oryzanol, 5-fluorouracil, bortezomib, or a combination thereof. Depending on the particular disease to be treated, the additional therapeutic agent or adjuvant may include drugs already known. In some embodiments, the additional therapeutic agent or adjuvant may include drugs that have already been clinically accepted to treat or prevent the disease.

In some embodiments, the pharmaceutical composition may comprise CBCBP and a pharmaceutically acceptable carrier or excipient. "Pharmaceutically acceptable carrier" or "pharmaceutically acceptable excipient" is intended to include any and all solvents, dispersion media, coatings, antibacterial and antifungal agents, isotonic and absorption delaying agents, and inert ingredients. The use of such pharmaceutically acceptable carriers or pharmaceutically acceptable excipients for active pharmaceutical ingredients is well known in the art. Except insofar as any conventional pharmaceutically acceptable carrier or pharmaceutically acceptable excipient is incompatible with the active pharmaceutical ingredient, its use in the therapeutic compositions of the invention is contemplated. Additional active pharmaceutical ingredients, such as other drugs, can also be incorporated into the described compositions and methods.

In yet another aspect, the amount of CBCBP in the pharmaceutical composition administered to a subject may be about 0.005 to 20 mg/kg body weight, about 0.005 to 10 mg/kg body weight, about 0.005 to 5 mg/kg body weight, about 0.005 to 2.5 mg/kg body weight, 0.01 to 20 mg/kg body weight, about 0.01 to 10 mg/kg body weight, about 0.01 to 5 mg/kg body weight, about 0.01 to 2.5 mg/kg body weight, 0.1 to 20 mg/kg body weight, about 0.1 to 10 mg/kg body weight, about 0.1 to 5 mg/kg body weight, or about 0.1 to 2.5 mg/kg body weight. The amount of CBCBP depends on the particular disease to be treated and the subject's specific conditions.

In yet another aspect, the administration of the pharmaceutical composition comprising CBCBP may last at least 1, 2, 3, 4, 5, 6, 7, 8, 9, 10, 11, 12, 13, 14, 21, 28, 35, 42, 49, 56, 63, 70, 77, 84, 91 or 98 days. In one embodiment, the administering of the pharmaceutical composition comprising CBCBP may last at least one week. In one embodiment, the administering of the pharmaceutical composition comprising CBCBP may last at least two weeks. The period of administration depends on the particular disease to be treated and the subject's specific conditions.

The present invention in various aspects and embodiments involves uses of CBCBP for the prevention or treatment of various diseases and methods of treating or preventing the diseases by administering a pharmaceutical composition comprising CBCBP. The diseases to be treated or prevented include but are not limited to cancers and viral infections.

In some embodiments, the disease is a cancer. In some embodiments, the cancer is selected from: bladder cancer, non-small cell lung cancer, cervical cancer, anal cancer, pancreatic cancer, squamous cell carcinoma including head and neck cancer, renal cell carcinoma, skin cancer, melanoma, ovarian cancer, small cell lung cancer, endometrial cancer, glioblastoma, astroycytoma, oligodendroglioma, ependymoma, neurofibrosarcoma, meningioma, gastrointestinal stromal tumor, breast cancer, lung cancer, colorectal cancer, thyroid cancer, bone sarcoma, stomach cancer, oral cavity cancer, oropharyngeal cancer, gastric cancer, kidney cancer, liver cancer, prostate cancer, esophageal cancer, testicular cancer, gynecological cancer, colon cancer, brain cancer, leukemia, lymphoma, leucocythemia, and multiple myeloma.

In some embodiments, the pharmaceutical composition comprising CBCBP may be used to prevent or treat prostate cancer, kidney cancer or leucocythemia. In one embodiment, the therapeutically effective amount of CBCBP to prevent or treat cancer is about 0.01 to about 10 mg/kg body weight. In another embodiment, the therapeutically effective amount of CBCBP to prevent or treat cancer is about 0.01 to about 5 mg/kg body weight.

In some embodiments, the disease is a viral infection. In some embodiments, the virus is a DNA virus or an RNA virus. For example, in some embodiments the virus may be a DNA virus such as but not limited to adenovirus, herpes simplex virus, human pepillomavrus, VITAMIN K virus, smallpox virus, hepatitis B virus (HBV), and parvovirus B19. In other embodiments, the virus may be an RNA virus such as but not limited to human astrovirus, norwalk virus, hepatitis A virus (HAV), severe acute respiratory syndrome virus, hepatitis C virus (HCV), yellow fever virus, dengue virus, West Nile virus, TBE virus, rubella virus, hepatitis E virus (HEV), human immunodeficiency virus (HIV), influenza virus, Lassa virus (LASV), Crimean-Congo hemorrhagic fever virus, Hantaan virus, Ebola virus, Marburg virus, Measles virus, mumps virus, parainfluenza virus, respiratory syncytial virus, rabies virus, and hepatitis D virus (HDV), rotavirus, orbivirus, coltivirus, Banna virus.

In some embodiments, the pharmaceutical composition comprising CBCBP may be used to prevent or treat viral infections caused by HBV, HCV, HIV or Hantaan virus. In one embodiment, the therapeutically effective amount of CBCBP to prevent or treat viral infection is about 0.01 to about 10 mg/kg body weight. In another embodiment, the therapeutically effective amount of CBCBP to prevent or treat cancer is about 0.01 to about 5 mg/kg body weight.

In some embodiments, the present invention provides a method of treating, preventing, reducing or alleviating the symptoms of, and/or slowing or halting the progress of prostate cancer, kidney cancer or leucocythemia in a subject in need thereof, the method comprising administrating to the subject an effective amount of a pharmaceutical composition comprising CBCBP. In one embodiment, the pharmaceutical composition consists of CBCBP. In some embodiments, the pharmaceutical composition further comprises at least one additional therapeutic agent or adjuvant. In a specific embodiment, the additional therapeutic agent or adjuvant may be selected from: folic acid, coenzyme Q10, curcumin, glutathione (GSH), aloe vera, oryzanol, 5-fluorouracil, and bortezomib. In one embodiment, the pharmaceutical composition comprises CBCBP and a pharmaceutically acceptable carrier or excipient.

In some embodiments, the present invention provides a method of treating, preventing, reducing or alleviating the symptoms of, and/or slowing or halting the progress of viral infections caused by HBV, HCV, HIV or Hantaan virus in a subject in need thereof, the method comprising administrating to the subject an effective amount of a pharmaceutical composition comprising CBCBP. In one embodiment, the pharmaceutical composition consists of CBCBP. In some embodiments, the pharmaceutical composition further comprises at least one additional therapeutic agent or adjuvant. In an embodiment, the additional therapeutic agent or adjuvant may be selected from: folic acid, coenzyme Q10, curcumin, glutathione (GSH), aloe vera, oryzanol, 5-fluorouracil, and bortezomib. In some embodiments, the pharmaceutical composition comprises CBCBP and a pharmaceutically acceptable carrier or excipient.

In some embodiments, for prevention or treatment of prostate cancer, kidney cancer or leucocythemia, the pharmaceutical composition comprising the CBCBP is administered with infusion, injections or via the oral route. In some embodiments, for prevention or treatment of prostate cancer, kidney cancer or leucocythemia, the pharmaceutical composition comprising the CBCBP is administered for at least one, two or three weeks.

In some embodiments, for prevention or treatment of viral infections caused by HBV, HCV, HIV or Hantaan virus, the pharmaceutical composition comprising the CBCBP is administered with infusion, injections or via the oral route. In one embodiment, for prevention or treatment of viral infections caused by HBV, HCV, HIV or Hantaan virus, the pharmaceutical composition comprising the CBCBP is administered for at least one, two or three weeks.

EXAMPLES

The following examples illustrate various embodiments of the present inventions and are not intended to limit the scope of the invention.

The effects of CBCBP on certain diseases can be demonstrated by results obtained from in vivo and in vitro studies. In addition, the process of making CBCBP and the physiochemical properties of CBCBP are also described.

The Effects of CBCBP on Prostate Cancer Cells

The co-crystal CBCBP was tested in the treatment of prostate cancers in comparison to docetaxel, a widely used drug in treating prostate cancer patients.

PC-3 cells are a cell line derived from advanced prostate cancer patient with bone metastasis and are characteristic of prostate cancer such as prostate small cell carcinoma. PC-3 cells were treated with drugs (CBCBP, docetaxel, or cisplatin) at step-wise concentrations, and the cell viability was evaluated with the CellTiter 96 AQueous One Solution Cell Proliferation Assay from Promega Corp. The index of cell growth repression ratio was obtained by comparing the OD490 data of treatment group to the negative control. The drug response rate $IC_{50}$ was calculated with the SPSS 16.0 system. The results are shown in FIG. 1.

CBCBP showed superior effect to reduce cell number compared to docetaxel. In particular, the $IC_{50}$ of CBCBP was 17.613 μM, while $IC_{50}$ of docetaxel and cisplatin were 49.924 μM and 2.489 μM respectively (FIG. 1).

LNCaP cells are a cell line derived from advanced prostate cancer patient with lymph node metastasis. LNCaP cells were treated with drugs (CBCBP, docetaxel, or cisplatin) at step-wise concentrations, and the cell viability was evaluated with the CellTiter 96 AQueous One Solution Cell Proliferation Assay from Promega Corp. The index of cell growth repression ratio was obtained by comparing the OD490 data of treatment group to the negative control. The drug response rate $IC_{50}$ was calculated with the SPSS 16.0 system. The results are shown in FIG. 2.

Figure 2:
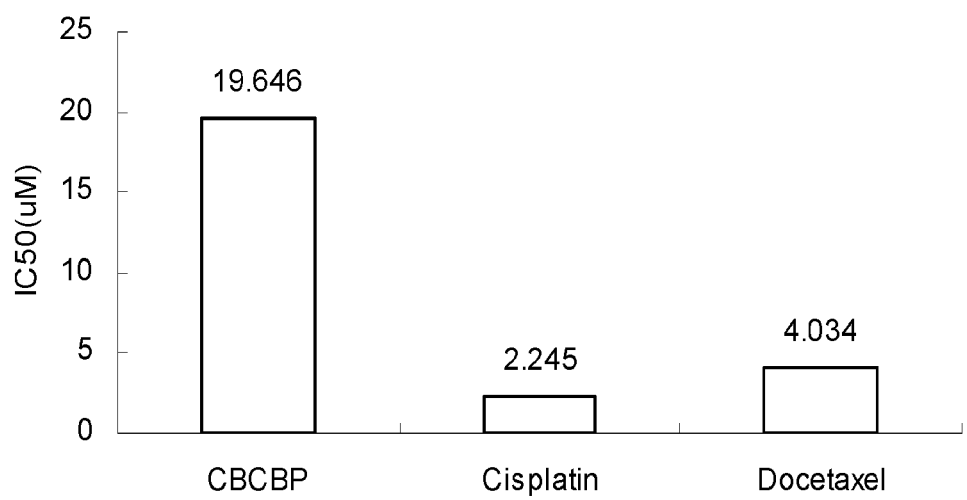
FIG. 2 shows the $IC_{50}$ of CBCBP and the control chemicals Docetaxel and cisplatin in LNCaP prostate cancer cell line.

For LNCaP cells, the $IC_{50}$ of CBCBP was 19.646μ M; the $IC_{50s}$ of docetaxel and cisplatin were 4.034 μM and 2.245 μM respectively (FIG. 2).

Figure 3:
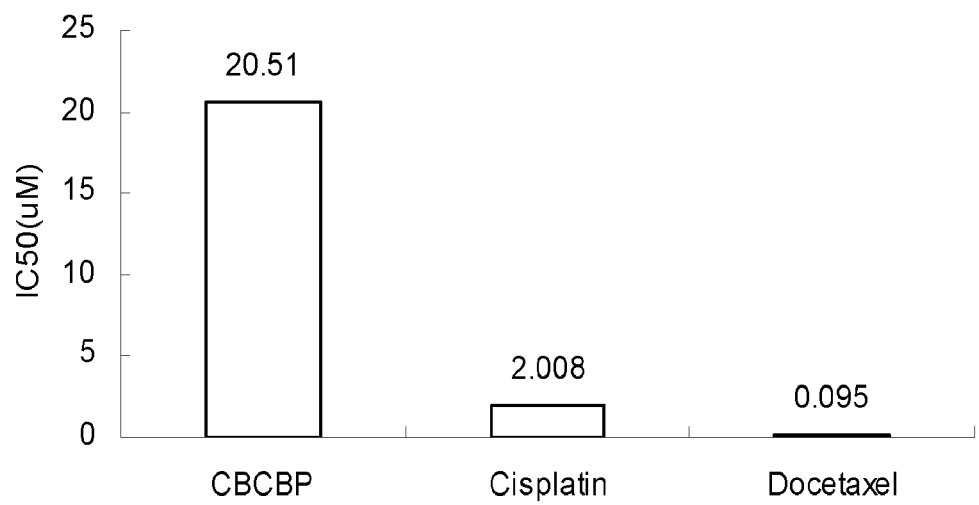
FIG. 3 shows the $IC_{50}$ of CBCBP and the control chemicals Docetaxel and cisplatin in fetal hepatocytes HL-7002.

HL-7002 cells are an immortalized human fetal hepatic cell line. HL-7002 cells were treated with drugs (CBCBP, docetaxel, or cisplatin) at step-wise concentrations, and the cell viability was evaluated with the CellTiter 96 AQueous One Solution Cell Proliferation Assay from Promega Corp. (Madison, Wis., USA). The index of cell growth repression ratio was obtained by comparing the OD490 data of treatment group to the negative control. The drug response rate $IC_{50}$ was calculated with the SPSS 16.0 system. The results are shown in FIG. 3.

For HL-7002 cells, CBCBP was detected to have minimum toxicity—about 1/216 of docetaxel and about 1/10 of cisplatin in similar conditions. The $IC_{50}$ of CBCBP was 20.51 µM; the $IC_{50}$ of docetaxel and cisplatin were 0.095 µM and 2.008 µM respectively (FIG. 3).

Figure 4:
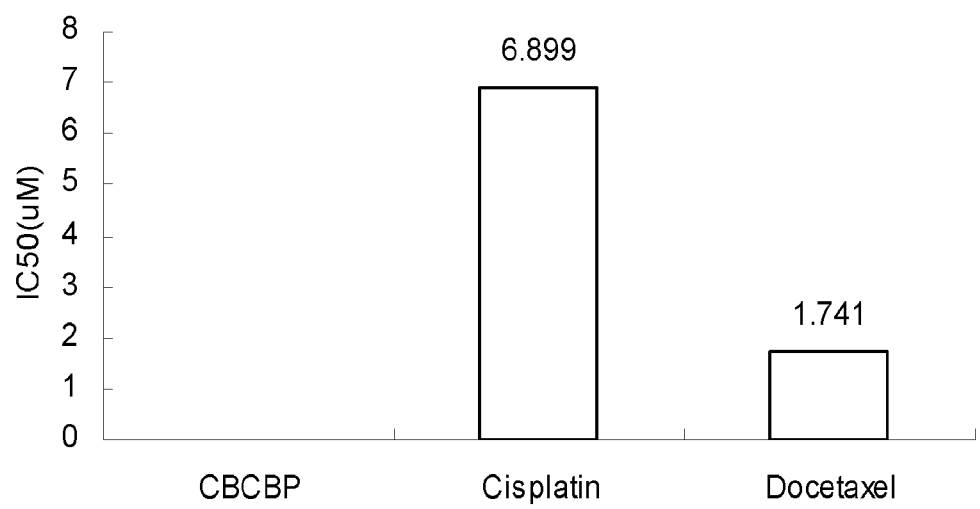
FIG. 4 shows the $IC_{50}$ of CBCBP and the control chemicals Docetaxel and cisplatin in human embryonic kidney cell line HEK293.

HEK293 cells are an immortalized human fetal kidney cell line. HEK293 cells were treated with drugs (CBCBP, docetaxel, or cisplatin) at step-wise concentrations, and the cell viability was evaluated with the CellTiter 96 AQueous One Solution Cell Proliferation Assay from Promega Corp. The index of cell growth repression ratio was obtained by comparing the OD490 data of treatment group to the negative control. The drug response rate $IC_{50}$ was calculated with the SPSS 16.0 system. The results are shown in FIG. 4.

For HEK293, no toxicity of CBCBP was detected, while docetaxel and cisplatin showed strong toxicity. The $IC_{50s}$ of docetaxel and cisplatin were 1.741 µM and 6.899 µM respectively (FIG. 4).

Methods:

Cell culture: Prostate cancer cell lines LNCaP and PC-3 were purchased from American Type Culture Collection (ATCC). The fetal hepatocytes HL-7002 and human embryonic kidney cells HEK393 were purchased from ATCC. The cells were cultured in RPMI+5% Fetal Bovine Serum (FBS).

Drug treatment and cell viability (MTS) assay: The cells (105/100 mL/well) were cultured in a 96 well plate, and treated with drugs (e.g. CBCBP) at step-wise concentrations from 0.01 to 300 µM. The cells treated with the solvents were used as the negative control, and cisplatin and docetaxel were used as the positive controls. The cells were monitored daily, and the cell viability was evaluated with the Promega CellTiter 96 AQueous One Solution Cell Proliferation Assay according to the manufacturer instructions. The cell viability was monitored at OD490 reading in a bio-spectrometer (Perkin Elmer).

Data analysis: The OD490 reading data were collected hourly from 1 h to 4 h after the addition of lysis buffer. The index of cell growth repression ratio was obtained by comparing the OD490 data of treatment to the negative control. The drug response rate $IC_{50}$ was calculated with the SPSS 16.0.

The Effects of CBCBP on Kidney Cancer Cells

The co-crystal CBCBP was tested in the treatment of kidney cancers in comparison to fluorouracil (5-FU), a widely used drug in treating kidney cancer patients.

Figure 5:
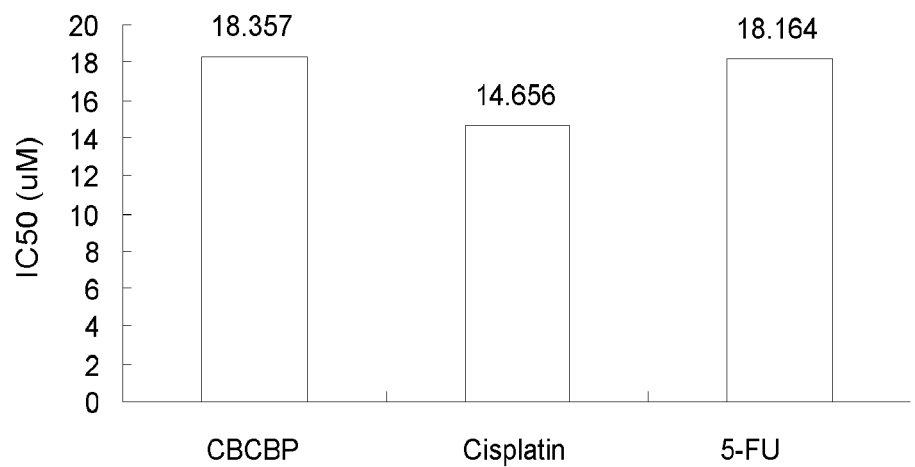
FIG. 5 shows the $IC_{50}$ of CBCBP and the control chemicals carboplatin and 5-FU in A498 kidney cancer cell line.

A498 cells are a kidney cancer cell line. A498 cells were treated with drugs (CBCBP, 5-FU, or cisplatin) at step-wise concentrations, and the cell viability was evaluated with the CellTiter 96 AQueous One Solution Cell Proliferation Assay from Promega Corp. The index of cell growth repression ratio was obtained by comparing the $OD_{490}$ data of treatment group to the negative control. The drug response rate $IC_{50}$ was calculated with the SPSS 16.0 system. The results are shown in FIG. 5.

For A498 cells, the effect to reduce cell number by CBCBP is comparable to 5-FU. $IC_{50}$ of CBCBP was 18.357 µM; $IC_{50s}$ of carboplatin and 5-FU were determined to be 14.656 µM and 18.164 µM respectively (FIG. 5).

Figure 6:
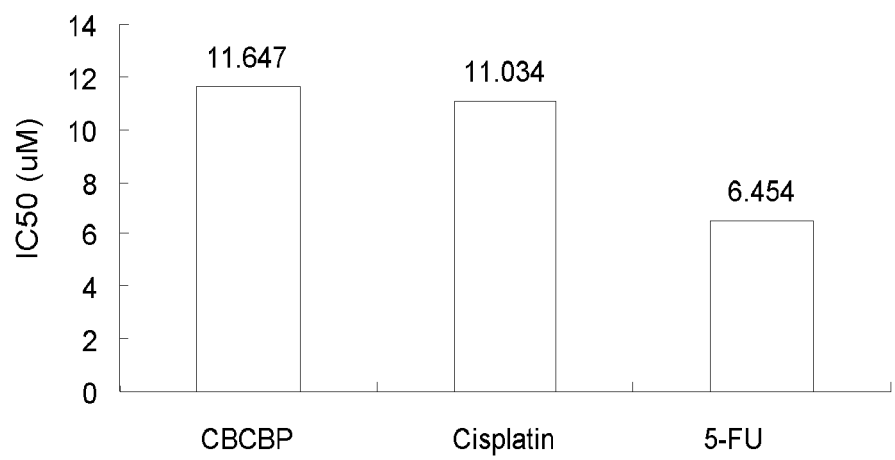
FIG. 6 shows the $IC_{50}$ of CBCBP and the control chemicals carboplatin and 5-FU in ACHN kidney cancer cell line.

ACHN cells are a kidney cancer cell line. ACHN cells were treated with drugs (CBCBP, 5-FU, or cisplatin) at step-wise concentrations, and the cell viability was evaluated with the CellTiter 96 AQueous One Solution Cell Proliferation Assay from Promega Corp. The index of cell growth repression ratio was obtained by comparing the $OD_{490}$ data of treatment group to the negative control. The drug response rate $IC_{50}$ was calculated with the SPSS 16.0 system. The results are shown in FIG. 6.

For ACHN cells, the effect to reduce cell number by CBCBP is comparable to carboplatin, $IC_{50}$ of CBCBP was 11.647 µM; $IC_{50}$ s of carboplatin and 5-FU were 11.034 µM and 6.454 µM respectively (FIG. 6).

Figure 7:
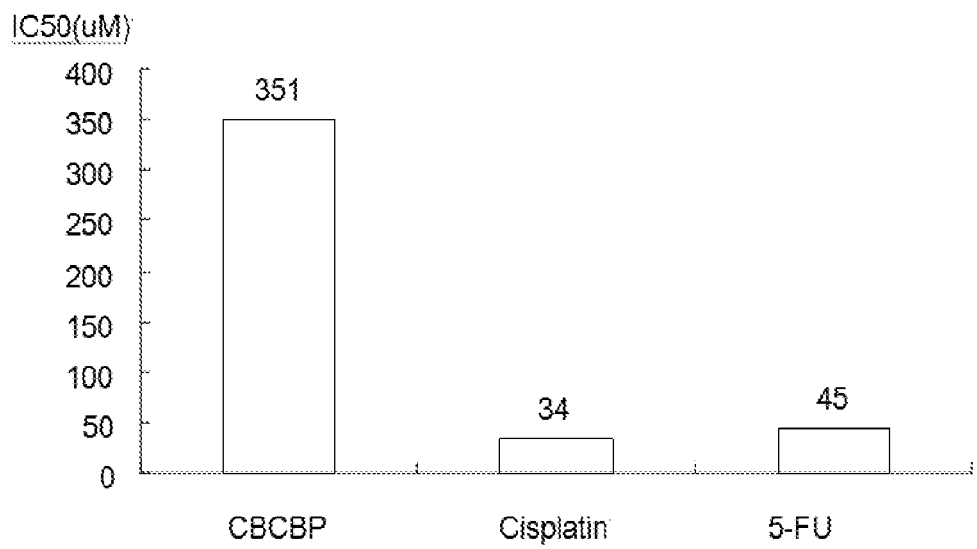
FIG. 7 shows the $IC_{50}$ of CBCBP and the control chemicals carboplatin and 5-FU in fetal hepatocytes HL-7002.

HL-7002 hepatocyte cell line cells were treated with drugs (CBCBP, 5-FU, or cisplatin) at step-wise concentrations, and the cell viability was evaluated with the CellTiter 96 AQueous One Solution Cell Proliferation Assay from Promega Corp. The index of cell growth repression ratio was obtained by comparing the $OD_{490}$ data of treatment group to the negative control. The drug response rate $IC_{50}$ was calculated with the SPSS 16.0 system. The results are shown in FIG. 7.

For HL-7002 cells, only minimum toxicity of CBCBP was detected. In similar conditions, the toxicity of CBCBP was about 1/10 of that of carboplatin and about 1/8 of that of 5-FU. $IC_{50}$ of CBCBP was 351 µM; $IC_{50}$ s of carboplatin and 5-FU were 34 µM and 45 µM respectively (FIG. 7).

Figure 8:
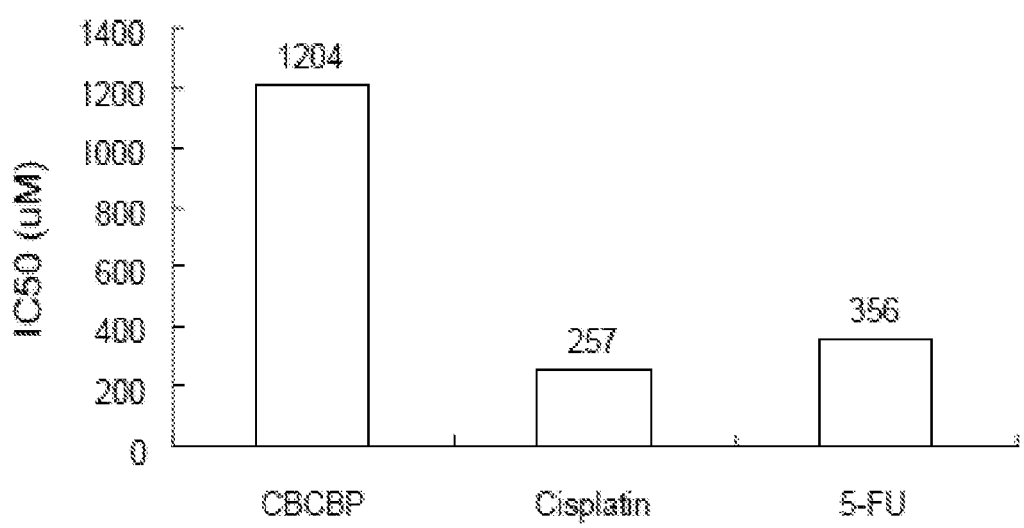
FIG. 8 shows the $IC_{50}$ of CBCBP and the control chemicals carboplatin and 5-FU in human embryonic kidney cell line HEK293.

HEK293 kidney cell line cells were treated with drugs (CBCBP, 5-FU, or cisplatin) at step-wise concentrations, and the cell viability was evaluated with the CellTiter 96 AQueous One Solution Cell Proliferation Assay from Promega Corp. The index of cell growth repression ratio was obtained by comparing the $OD_{490}$ data of treatment group to the negative control. The drug response rate $IC_{50}$ was calculated with the SPSS 16.0 system. The results are shown in FIG. 8.

For HEK293, only minimum toxicity of CBCBP was detected. In similar conditions, the toxicity of CBCBP was about 1/5 of that of carboplatin and about 1/4 of that of 5-FU. $IC_{50}$ of CBCBP was 1204 µM; $IC_{50}$ s of $IC_{50}$ of carboplatin and 5-FU were 237 µM and 356 µM respectively (FIG. 8).

Methods

Cell culture: Kidney cancer cell lines A498 and ACHN were purchased from Tongmai Biotech (Shanghai, China). The fetal hepatocytes HL-7002 and human embryonic kidney cells HEK393 were purchased from ATCC, The cells were cultured in RPMI+5% Fetal Bovine Serum (FBS).

Drug treatment and cell viability (MTS) assay: The cells (105/100 mL/well) were cultured in 96 well plate, and treated with drugs (e.g. CBCBP) at a step-wise concentrations from 0.01 uM to 300 uM. The cells treated with the solvents were used as the negative control, and carboplatin and 5-FU were used as the positive controls. The cells were monitored daily, and the cell viability was evaluated with the Promega CellTiter 96 AQueous One Solution Cell Proliferation Assay (Promega) according to the manufacture manuals. The cell viability was monitored at OD490 reading in a bio-spectrometer (Perkin Elmer).

Data analysis: The $OD_{490}$ reading data were collected hourly from 1 to 4 h after the addition of lysis buffer. The index of cell growth repression ratio was obtained by comparing the OD490 data of treatment to the negative control. The drug response rate $IC_{50}$ was calculated with the SPSS 16.0.

The Effects of CBCBP on Virus Infections

CBCBP is effective to reduce infection with DNA viruses, RNA viruses and retroviruses. The effects of CBCBP on Hantaan virus (HTNV) and hepatitis B virus (HBV) were examined. It was found that CBCBP showed low toxicity on normal cells and moderate activity as an anti-virus agent. Preliminary studies indicated that additional therapeutic agent or adjuvant is of essence in promoting activity and lower the toxicity, additional therapeutic agent or adjuvant may be folic acid, coenzyme Q10, curcumin, glutathione (GSH), aloe vera, oryzanol, 5-fluorouracil, bortezomib, or a combination thereof.

Anti-HTNV Effects of CBCBP on VeroE6 Cells

VeroE6 cells infected with HTNV were treated with CBCBP. The percentage of infected cells was calculated by comparing the virus-infected cells with all cells in each field, and the IC50 was calculated according to a regression equation. The $IC_{50}$ of CBCBP is 33.684 μg/mL. The results are show in Table 1.

TABLE 1

Effect of CBCBP concentration on the inhibition of HTNV

| Time | concentration (μg/mL)/inhibition rate (%) | | | | | $IC_{50}$ |
|---|---|---|---|---|---|---|
| (d) | 2.3 | 4.6 | 9.3 | 18.7 | 37.5 | (μg/mL) |
| 7 | 6.5 | 20.0 | 25.5 | 40.0 | 50.0 | 33.684 |

The $TC_{50}$ of CBCBP on VeroE6 cells is 58.367 μg/mL by comparing with the effects of cellular toxicity and anti-HNTV of three chemicals. All tested chemicals showed significant anti-HNTV effect with a dose-effect relationship.

The Effects of CBCBP on HBV Antigens Secreted by HepG2.2.15 Cells

The levels of HbsAg and HbeAg in chemical-treated HepG2.2.15 cells were detected by enzyme-linked immunosorbent assay (ELISA). As shown in Table 2, the effects of CBCBP on HBsAg level secreted by HepG2.2.15 cells indicated inhibition on HBsAg and HBeAg.

TABLE 2

Influence of CBCBP on HBV antigens secreted by HepG2.2.15 cells

| HBV | | concentration (μg/mL)/inhibition rate (%) | | | | $ID_{50}$ |
|---|---|---|---|---|---|---|
| antigens | | 3.125 | 6.25 | 12.5 | 25 | (μg/mL) |
| HbsAg | 3d | 19.5 | 23.6 | 37.3 | 48.5 | 36.303 |
| HbeAg | 3d | 0.6 | 25.0 | 25.3 | 28.5 | 67.311 |

Preparation of CBCBP

CBCBP was formed from carboplatin and 1,2-cis-cyclobutane dicarboxylate as co-crystal formers. A comprehensive co-crystal screening was performed via slurry/stirring, heating and cooling, rotary evaporation, lyophilization, cooling, and evaporation. One co-crystal was obtained and named as co-crystal Form A.

As per single crystal structure analysis, CBCBP consists of carboplatin and cis-cyclobutane-1, 2-dicarboxylic acid with molar ratio of 1:1. As a result, the co-crystal was prepared and its structure was designated as Form A. Meanwhile its single crystal was obtained and characterized. Form A was characterized by X-ray powder diffraction pattern (XRPD) (FIG. 9), thermogravimetric analysis (TGA) and differential scanning calorimetry (DSC) (FIG. 10). Analysis of the single crystal showed that Form A is a co-crystal of carboplatin and 1,2-cis-cyclobutane dicarboxylatein a 1:1 ratio. XRPD of the Form A was demonstrated in FIG. 9. TGA indicated that weight loss is 6.4% when heating to 150° C., while DSC showed obvious absorption at 46.4° C. and 174.5° C.

Cooling and lyophilization methods were scaled up to prepare co-crystal Form A. Molar ratio of starting materials and rinsing method were optimized. Several hundred milligrams of co-crystal were obtained.

As shown in FIG. 11, different ratio of co-crystal formers leads to the formation of the form A in a different quality (method A). The preferred ratio of carboplatin to 1,2-cis-cyclobutane dicarboxylate is 1:11. When CBCBP was prepared by cooling-dry method (method B), washing with water and EtOH/Heptane is of significance to get high quality co-crystal.

Specifically, CBCBP was produced with Method A: 120.0 mg of carboplatin, 512.4 mg of 1,2-cis-cyclobutane dicarboxylate and 0.5 mL of distilled water were stirred around 30° C. for 0.5 hour; then the obtained solution was cooled to 5° C. overnight; the mixtures were treated with centrifugation and about 30 mg of the crystal compound was obtained; yield was about 18%.

The resulting product was analyzed by XRPD, DSC/TGA and proton nuclear magnetic resonance (H-NMR). In addition, the resulting CBCBP was observed with scanning electron microscopy (SEM) (FIG. 21, FIG. 22, and FIG. 23).

CBCBP was also produced with Method B: 555.8 mg of carboplatin, 494 mg of 1,2-cis-cyclobutane dicarboxylate and 0.1 mL of distilled water were stirred around 30° C. for 0.5 hour; then the obtained solution was filtered through 0.45 um filter and the solution was dried by cooling; as a result of cooling dry, about 770 mg of crude co-crystal was obtained; the crude crystal was treated with ethanol and heptane and 448 mg of pure crystal was obtained and cooled to 5° C. overnight. The resulting product was analyzed by XRPD, DSC/TGA, H-NMR and SEM, with the same findings as the resulting product of Method A.

Characterization of CBCBP

Analysis of the single crystal forms revealed the chemical structure of CBCBP. As shown in FIG. 15 and FIG. 16, it appeared that 1:1 ratio of carboplatin and 1,2-cis-cyclobutane dicarboxylate were present in the co-crystal.

Suitable single crystals of CBCBP were obtained by slow evaporation in water at 4° C. with seeding. Structure determination using one of these single crystals was carried out and the results are shown in FIG. 17, FIG. 18, FIG. 19 and FIG. 20. The structure confirmed a 1:1 co-crystal. cyclobutane-1, 2-dicarboxylic acid is in the cis isomer. Carboplatin and cis-cyclobutane-1,2-dicarboxylic acid are involved in hydrogen bonds (N—H . . . O, O—H . . . O and O—H . . . N). A two dimensional structure along crystallographic ab plane is formed through intermolecular hydrogen bonds.

The crystal structure of carboplatin cis-cyclobutane-1,2-dicarboxylic acid co-crystal has been successfully determined using a set of diffraction data collected from a single crystal (807604-10-A3). The crystal data and structure refinement are listed in Table 3.

TABLE 3

Crystal data and structure refinement for single crystal of CBCBP

| | | |
|---|---|---|
| Identification code | CP2758 | — |
| Empirical formula | $C_{12}H_{18}N_2O_8Pt$ | — |
| Formula weight | 513.37 | — |
| Temperature | 296(2) | — |

TABLE 3-continued

| Crystal data and structure refinement for single crystal of CBCBP | | |
|---|---|---|
| Wavelength | 0.71073 Å | — |
| Crystal system, space group | Monoclinic | $P2_1/c$ |
| Unit cell dimensions | a = 5.5860(11) Å | α = 90 deg. |
| | b = 11.488(2) Å | β = 92.079(4) deg. |
| | c = 25.167(5) Å | γ = 90 deg. |
| Volume | 1614.0(5) Å$^3$ | — |
| Z, Calculated density | 4 | 2.113 Mg/m$^3$ |
| Absorption coefficient | 8.736 mm$^{-1}$ | — |
| F(000) | 984 | — |
| Crystal size | 0.28 × 0.25 × 0.10 mm$^3$ | — |
| Theta range for data collection | 1.95 to 27.59 deg. | — |
| Limiting indices | −7 ≤ h ≤ 7 | — |
| | −14 ≤ k ≤ 14 | |
| | −32 ≤ l ≤ 26 | |
| Reflections collected/unique | 9905/3677 [R(int) = 0.0418] | — |
| Completeness | 98.2% | — |
| Refinement method | Full-matrix least-squares on F$^2$ | — |
| Data/restraints/parameters | 3677/5/221 | — |
| Goodness-of-fit on F$^2$ | 1.157 | — |
| Final R indices [I > 2sigma(I)] | $R_1$ = 0.0873 | $wR_2$ = 0.1901 |
| Largest diff. peak and hole | 3.081 and −5.807 e.Å$^{-3}$ | — |

Figure 15:
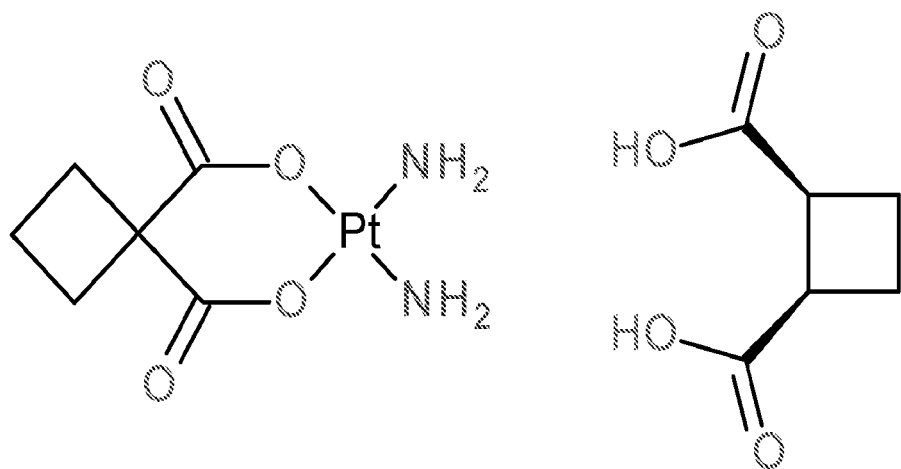
FIG. 15 shows the chemical structure of CBCBP.
Figure 16:
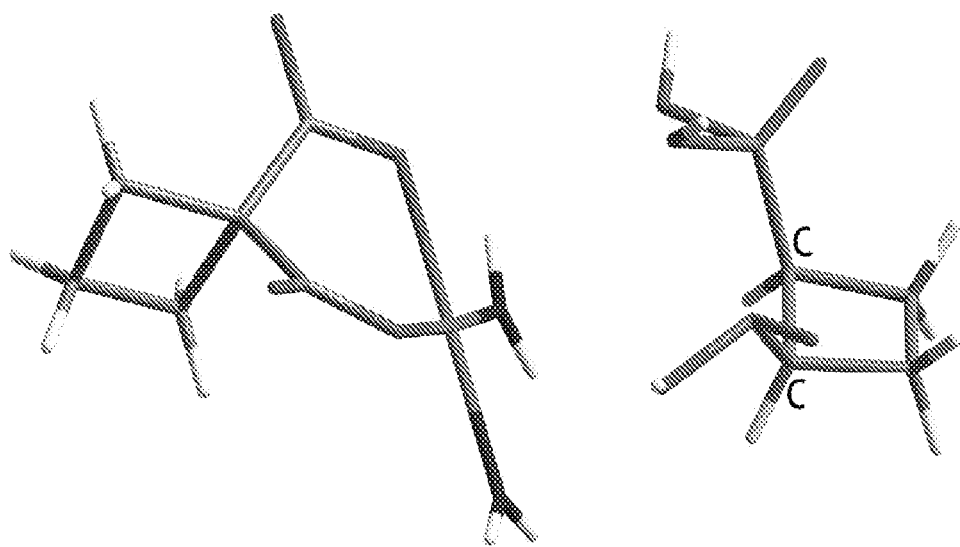
FIG. 16 shows the three-dimensional structure of single crystal of CBCBP.
Figure 17:
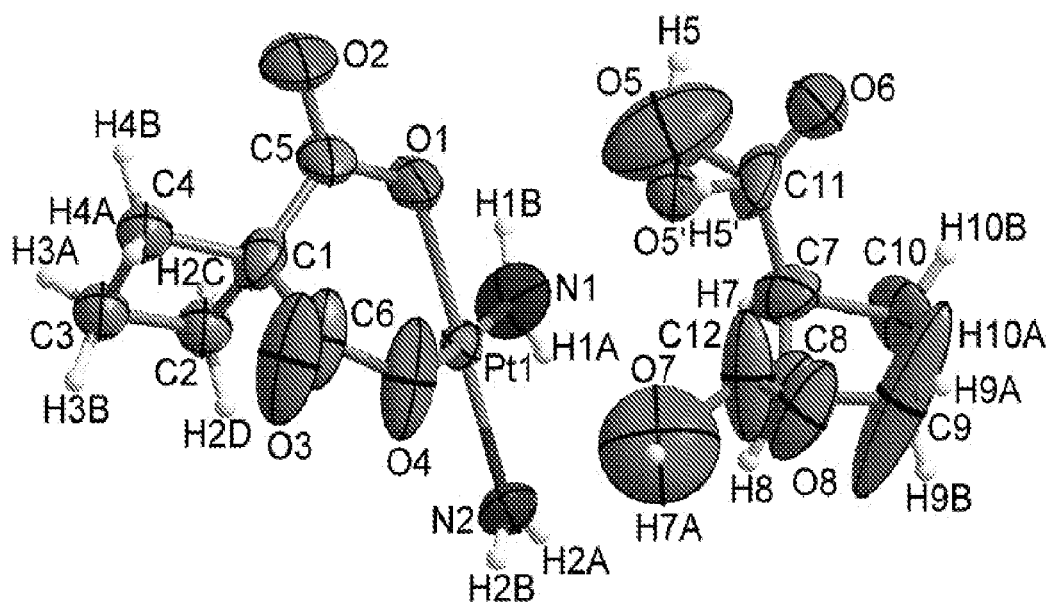
FIG. 17 shows the illustrated glossary of organic chemistry (ORTEP) diagram of a single crystal of CBCBP (50% probability).
Figure 18:
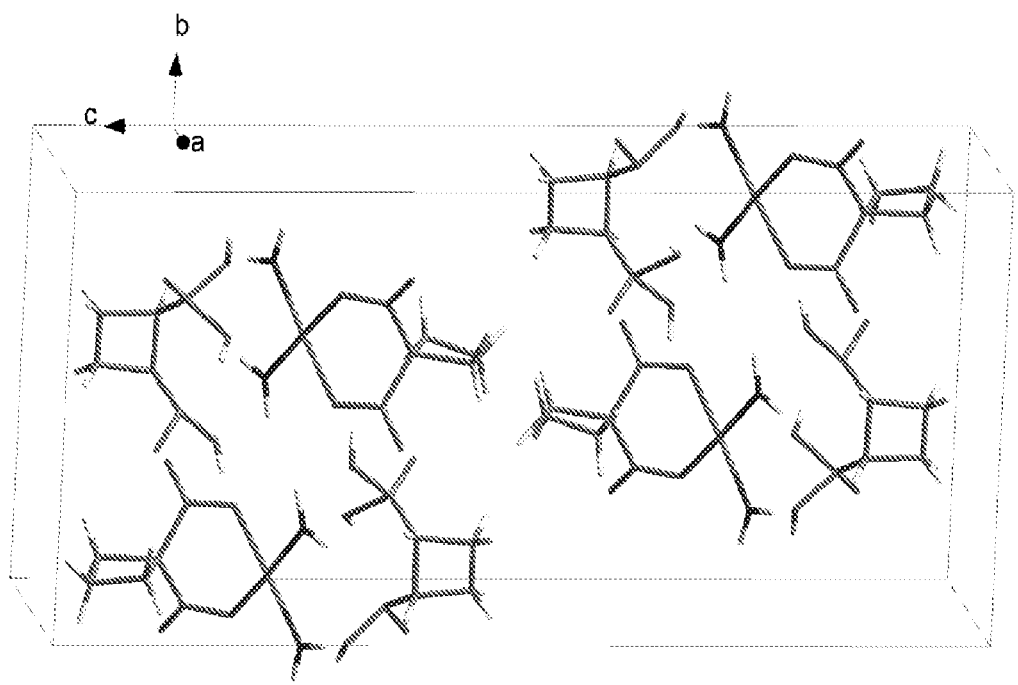
FIG. 18 shows the unit cell of single crystal of CBCBP.

The absolute structure of CBCBP is shown in FIG. 15. FIG. 16 shows the molecular structure of CBCBP. Cyclobutane-1,2-dicarboxylic acid was confirmed to be in cis configuration (FIG. 16). An ORTEP drawing of the crystal structure is shown in FIG. 17. One oxygen atom is disordered over two positions (O5 and O5') with a ratio of 0.5 to 0.5. The crystal structure confirmed a 1:1 co-crystal with four carboplatin and four cis-cyclobutane-1,2-dicarboxylic acid molecules in one unit as shown in FIG. 18.

Figure 13:
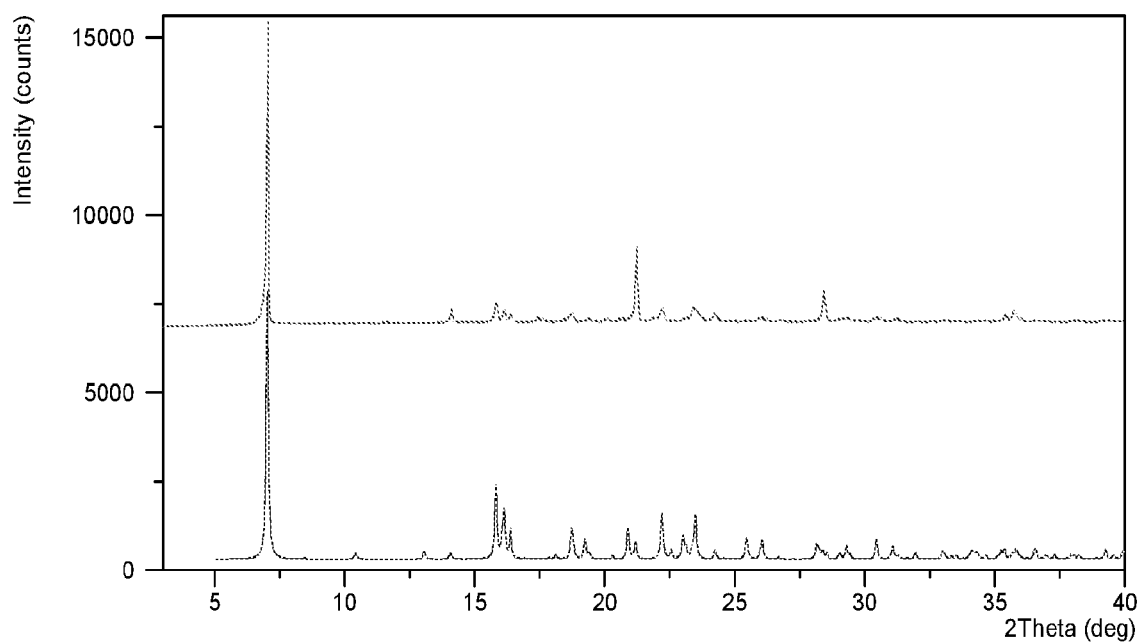
FIG. 13 shows the simulated and experimental (807603-23-A1) XRPD patterns of a CBCBP sample.
Figure 14:
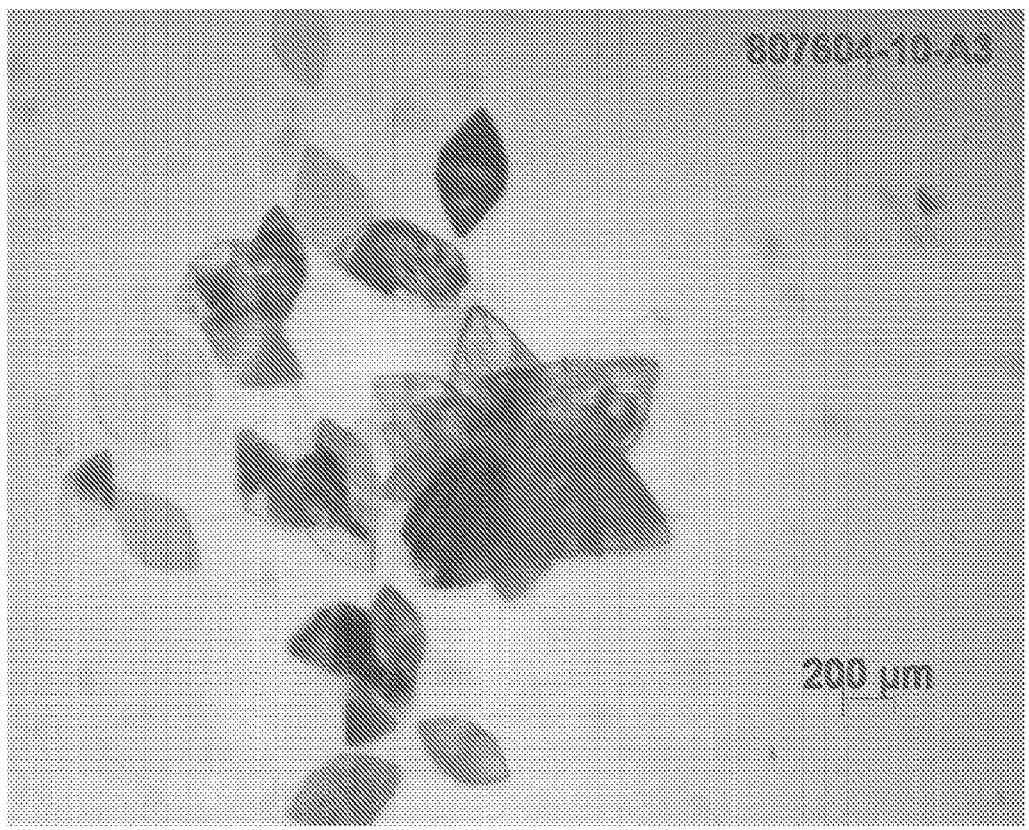
FIG. 14 shows the image of single crystals (807604-10-A3) of a CBCBP sample.
Figure 19:
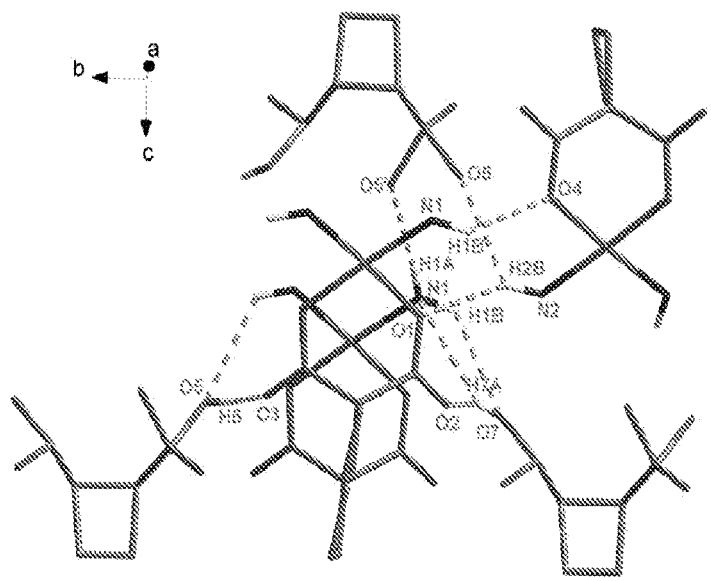
FIG. 19 shows the hydrogen bonds of single crystal of CBCBP (H atoms are omitted for clarity).
Figure 20:
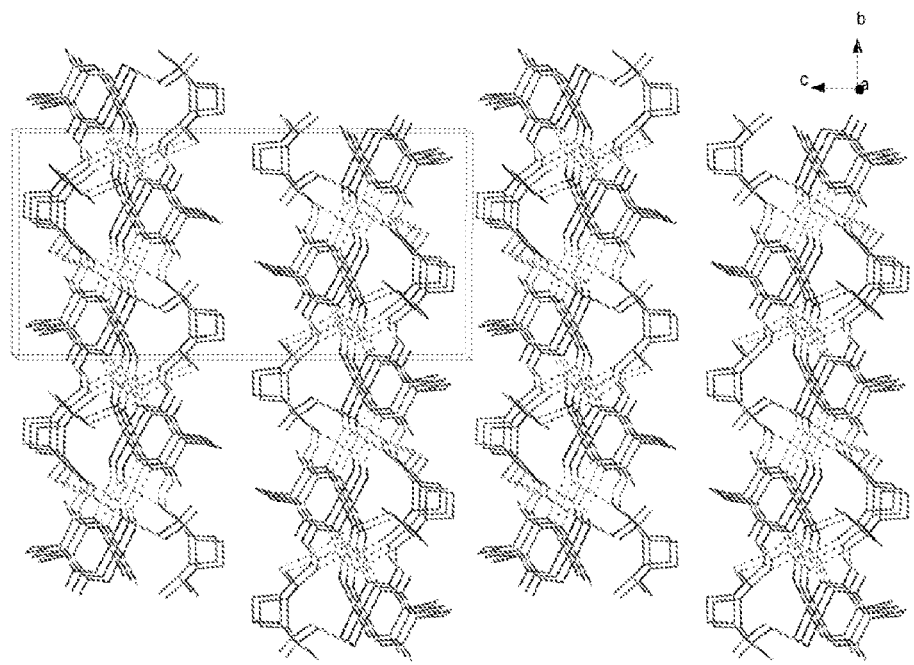
FIG. 20 shows the crystal packing of single crystal of CBCBP (H atoms are omitted for clarity).
Figure 21:
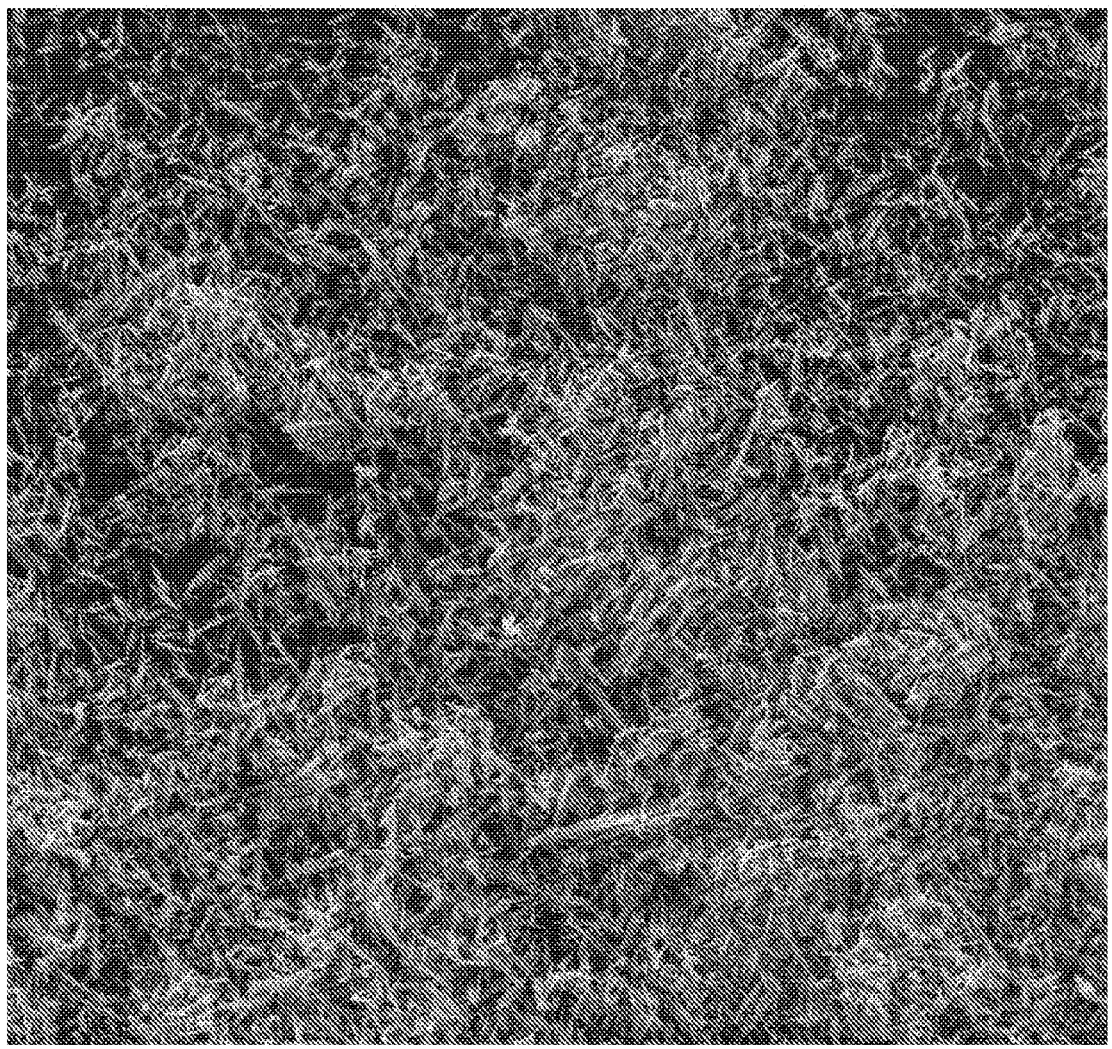
FIG. 21 shows the SEM (scanning electron mircroscope) results of a CBCBP sample.
Figure 22:
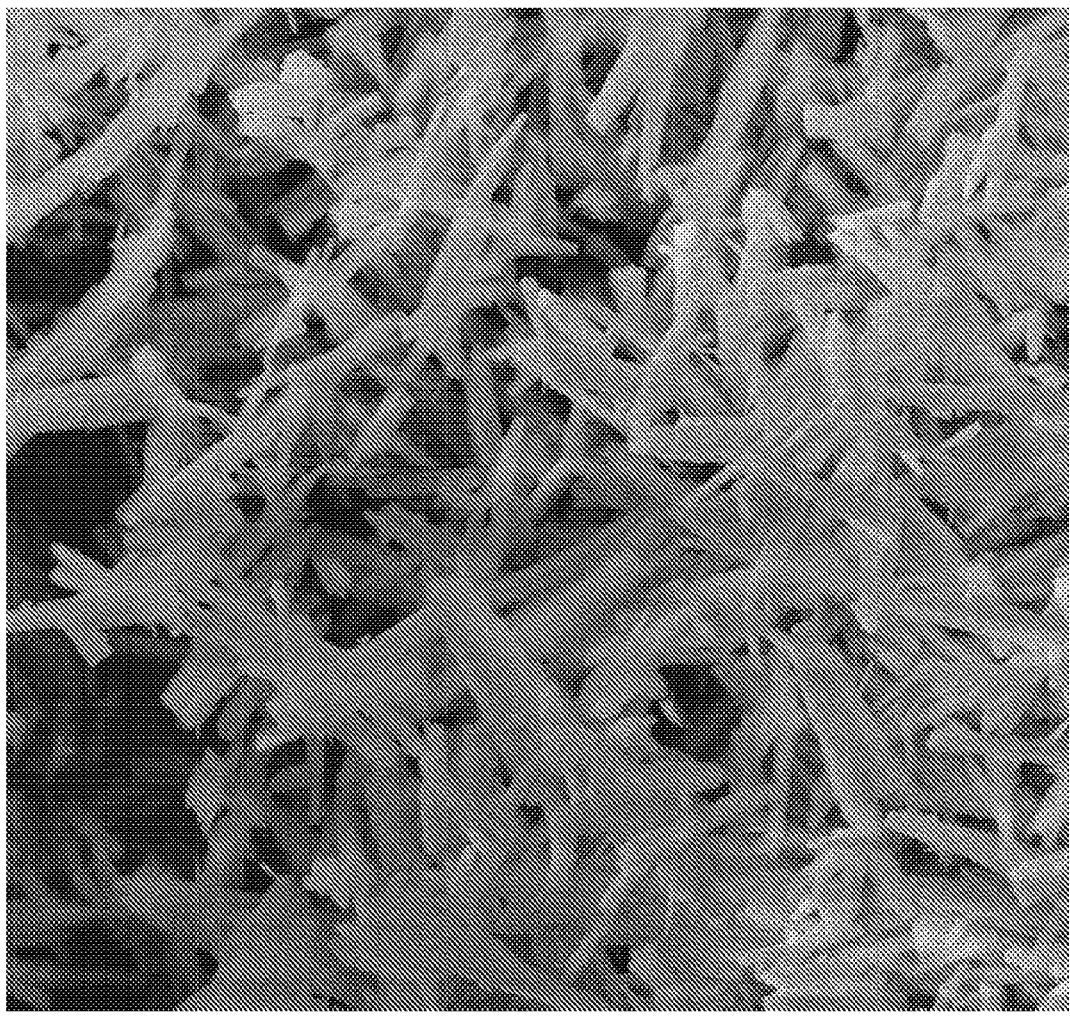
FIG. 22 shows the SEM results of a CBCBP sample.
Figure 23:
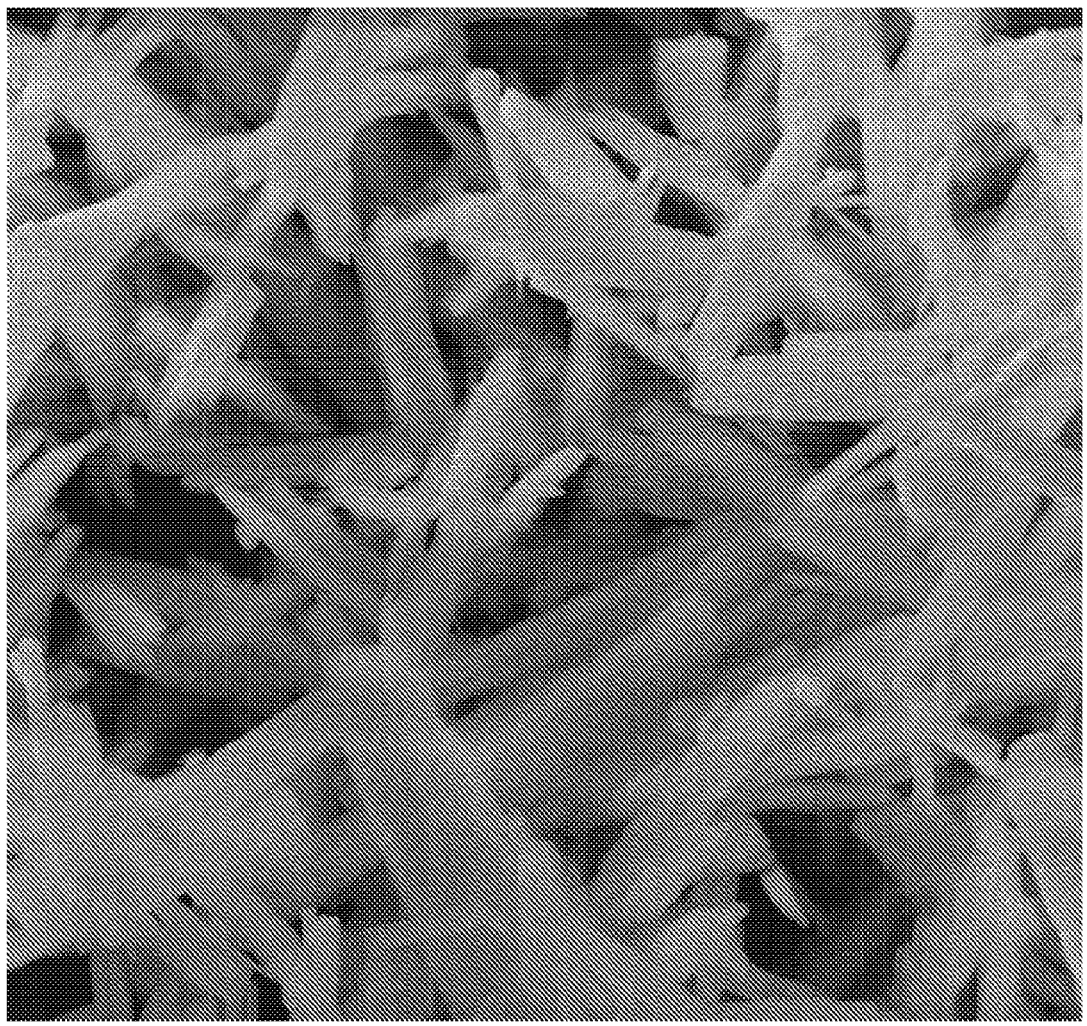
FIG. 23 shows the SEM results of a CBCBP sample.

In the structure, carboplatin and cis-cyclobutane-1,2-dicarboxylic acid are involved in hydrogen bonds (N—H . . . O, O—H . . . O and O—H . . . N). The hydrogen bonding interactions are demonstrated in FIG. 19. A two dimensional structure along crystallographic ab plane is formed through intermolecular hydrogen bonds as indicated by the crystal packing shown in FIG. 20. The theoretical XRPD pattern calculated from the single crystal structure matches well with the experimental one (807603-23-A1) as demonstrated in FIG. 13.

Analytical Methods

X-ray Powder Diffraction (XRPD):

Polarized light microscopic picture was captured at room temperature (RT). X-ray intensity data were collected at 296(2) K using a Bruker APEX II CCD diffractometer (Mo Kα radiation, λ=0.71073 Å). XRPD pattern was collected by Panalytical Empyrean system at RT. Direct methods structure solution, difference Fourier calculations and full-matrix least-squares refinement against F2 were performed with SHELXTL and OLEX2, See Sheldrick, *Acta Crystallographica A*, 64: 112-122, 2008; and Dolomanov, *J. Appl. Cryst.* 42, 339-341, 2009; and Brandenburg, *DIAMOND*, 1999, Crystal Impact GbR, Bonn, Germany. Molecular graphics were created according to Brandenburg, K. *DIAMOND*, 1999, Crystal Impact GbR, Bonn, Germany.

Analytical Instrument: Panalytical Empyrean. The X-ray powder diffraction was conducted by mounting a sample of the crystalline material on a Si single crystal low-background holder and spreading out the sample into a thin layer with the aid of a microscope slide. The 2θ position was calibrated against Panalytical 640 Si powder standard. The sample was irradiated with X-rays generated by a copper long-fine focus tube operated at 45 kV and 40 mA with a wavelength of Kα1=1.540589 angstroms and Kα2=1.544426 angstroms (Kα2/Kα1 intensity ratio is 0.50). The collimated X-ray source was passed through a programmed divergence slit set at 10 mm and the reflected radiation directed through a 5.5 mm anti-scatter slit. The sample was exposed for 16.3 seconds per 0.013° 2-theta increment (continuous scan mode) over the range 3 degrees to 40 degrees 2-theta in theta-theta mode. The running time was 3 minutes and 57 seconds. The instrument was equipped with a RTMS detector (X'Celerator). Control and data capture was by means of a Dell Optiplex 780 XP operating with data collector software.

Persons skilled in the art of X-ray powder diffraction will realize that the relative intensity of peaks can be affected by, for example, grains above 30 microns in size and non-unitary aspect ratios that may affect analysis of samples. The skilled person will also realize that the position of reflections can be affected by the precise height at which the sample sits in the diffractometer and the zero calibration of the diffractometer. The surface planarity of the sample may also have a limited effect. Hence the diffraction pattern data presented are not intended to be limited to the absolute values.

Differential Scanning calorimetry (DSC)

DSC was used as a thermoanalytical method to measure the difference in the amount of heat required to increase the temperature of a sample and reference was measured as a function of temperature. The general process of DSC is known and the specific instruments and conditions in the following Examples were as follows:

Analytical Instrument: TA Instruments Q2000 DSC;

Heating rate: 10° C. per minute; and Purge gas: nitrogen.

5.3 Thermal Gravimetric Analysis (TGA)

TGA was used to measure changes in physical and chemical properties of samples as a function of increasing temperature (with constant heating rate), or as a function of time (with constant temperature and/or constant mass loss). The general process of TGA is known and the specific instruments and conditions in the following Examples were as follows:

Analytical Instrument: TA Instruments Q5000 TGA;

Heating rate: 10° C. per minute; and

Purge gas: nitrogen.

Sample Pharmaceutical Composition Comprising CBCBP and Administration

Aqueous or solid pharmaceutical composition of the present invention comprises an effective amount of CBCBP, with or without an appropriate amount of at least one additional therapeutic agent or adjuvant. CBCBP, as well as the therapeutic agent or adjuvant, may be dissolved or dispersed in a pharmaceutical acceptable carrier or aqueous media.

Depending on the particular cancer to be treated, administration of pharmaceutical composition according to the present invention can via any common route as long as the target issue is available via the route. For example, the pharmaceutical composition may be administered by infusion, injection, or via the oral route.

A number of pharmaceutical compositions were produced:

Pharmaceutical composition sample A: 70 g of CBCBP was dissolved in pre-treated normal saline or 5% of aqueous glucose (in water) and the final volume of the solution was adjusted to 5.0 L. Then the solution was filtered through 0.22 um filter and dispersed into ample bottles with 50.0 mL in each.

Pharmaceutical composition sample B: 70 g of CBCBP and 20 g of glutathione (GSH) were dissolved in pre-treated normal saline or 5% aqueous glucose (in water) and final volume of the solution was adjusted to 5.0 L of solution. Then the solution was filtered through 0.22 um filter and dispersed into ample bottle with 50.0 mL solution each.

Pharmaceutical composition sample C: 70 g of CBCBP, 20 g of glutathione (GSH), 1400 g of curcumin and 20 g of coenzyme Q10 were mixed evenly. The mixture was evenly distributed into 14,000 capsules.

What is claimed is:

1. A co-crystal having a structure of formula (I):

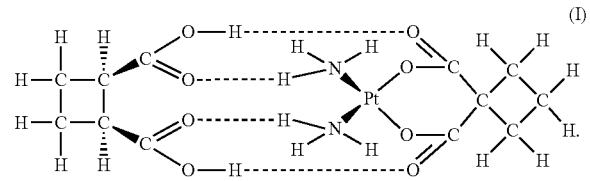

wherein the co-crystal is in form A.

Figure 9:
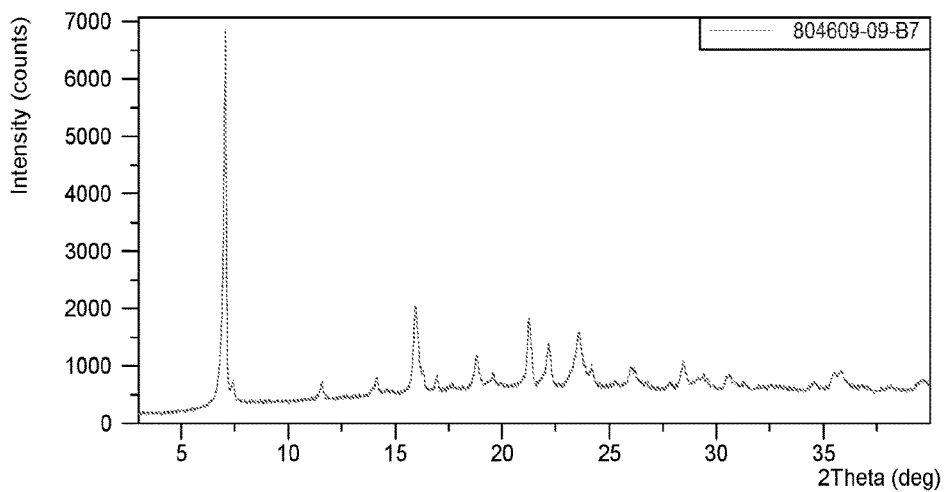
FIG. 9 shows the X-ray powder diffraction (XRPD) pattern of form A of CBCBP.
Figure 10:
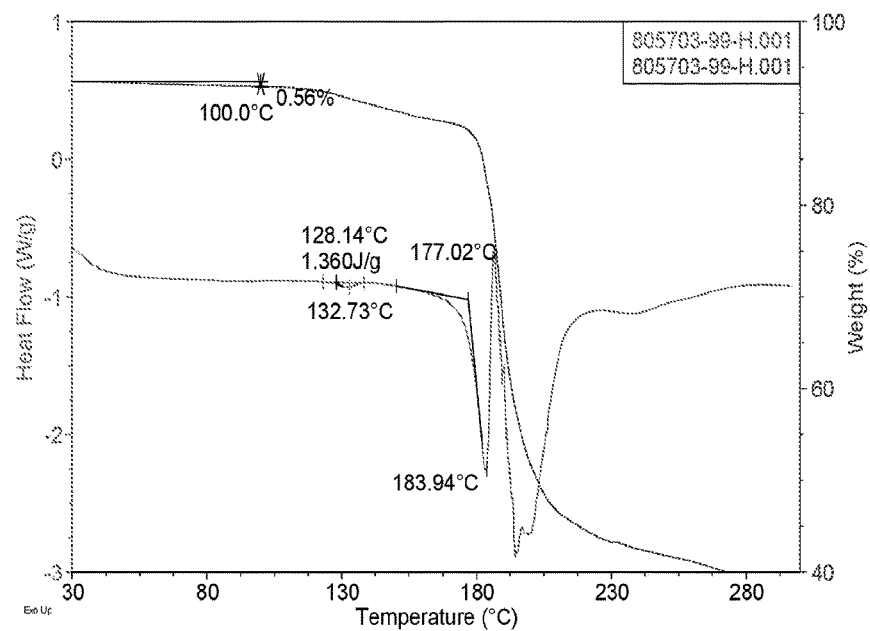
FIG. 10 shows the TGA/DSC of a CBCBP sample formed by cooling-dry (sample ID: 805703-99-H).
Figure 11:
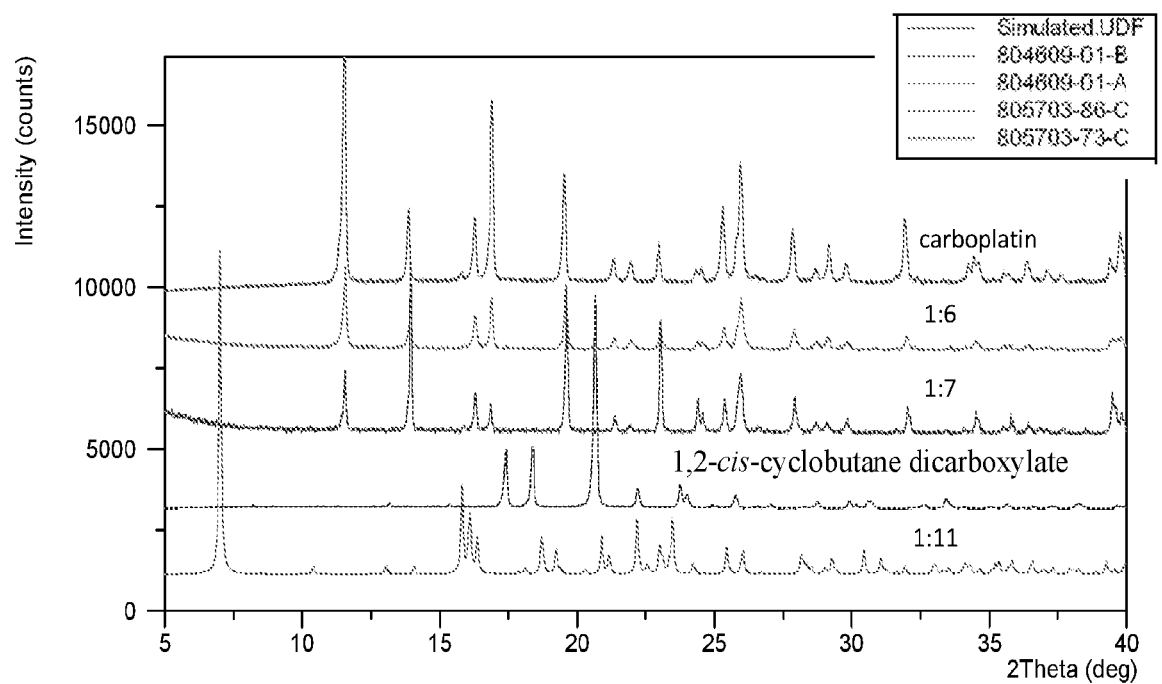
FIG. 11 shows the XRPD of Form A of CBCBP at different ratio of co-crystal formers (ratio: carboplatin to acid).
Figure 12:
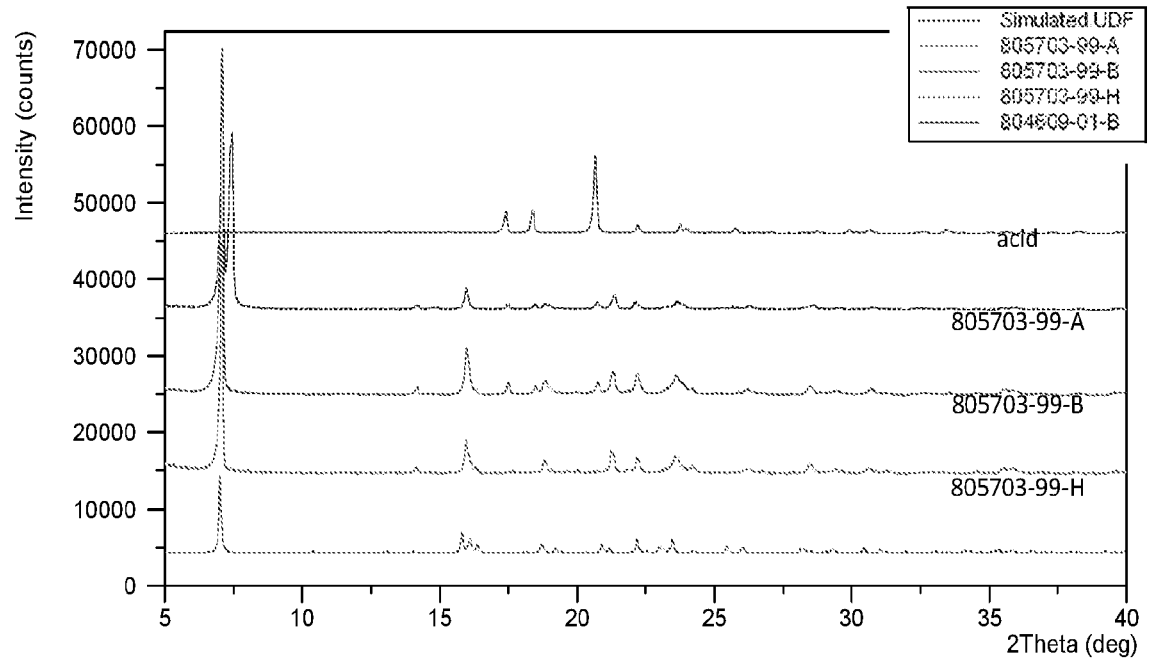
FIG. 12 shows the XRPD of CBCBP samples prepared by cooling-dry (acid: 1,2-cis-cyclobutane dicarboxylate; 805703-99-A: crude co-crystal; 805703-99-B: washed with water; 805703-99-H: washed with EtOH/Heptane).

2. The co-crystal of claim 1, wherein the co-crystal is characterized by an XRDP as shown in FIG. 9.

3. A pharmaceutical composition comprising the co-crystal of claim 1 dissolved or dispersed in a pharmaceutically acceptable carrier or aqueous media.

4. The pharmaceutical composition of claim 3, further comprising at least one therapeutic agent or adjuvant.

5. The pharmaceutical composition of claim 4, wherein the therapeutic agent or adjuvant is selected from the group consisting of folic acid, coenzyme Q10, curcumin, glutathione (GSH), aloe vera, oryzanol, 5-fluorouracil, and bortezomib.

6. A method of treating cancer in a subject in need thereof, comprising administering to the subject the pharmaceutical composition of claim 3, wherein the co-crystal is present in a therapeutically effective amount.

7. The method of claim 6, wherein the cancer is selected from: bladder cancer, non-small cell lung cancer, cervical cancer, anal cancer, pancreatic cancer, squamous cell carcinoma including head and neck cancer, renal cell carcinoma, skin cancer, melanoma, ovarian cancer, small cell lung cancer, endometrial cancer, glioblastoma, astroycytoma, oligodendroglioma, ependymoma, neurofibrosarcoma, meningioma, gastrointestinal stromal tumor, breast cancer, lung cancer, colorectal cancer, thyroid cancer, bone sarcoma, stomach cancer, oral cavity cancer, oropharyngeal cancer, gastric cancer, kidney cancer, liver cancer, prostate cancer, esophageal cancer, testicular cancer, gynecological cancer, colon cancer, brain cancer, leukemia, lymphoma, leucocythemia, and multiple myeloma.

8. The method of claim 6, wherein the cancer is selected from the group consisting of prostate cancer, kidney cancer and leucocythemia.

9. The method of claim 6, wherein the pharmaceutical composition is an aqueous composition comprising an effective amount of the co-crystal and pharmaceutically acceptable amount of at least one therapeutic agent or adjuvant dissolved or dispersed in a pharmaceutically acceptable carrier or aqueous media.

10. The method of claim 6 wherein the pharmaceutical composition is administered via infusion, injection or the oral route.

11. A method of treating a virus infection in a subject in need thereof, comprising administering to the subject the pharmaceutical composition of claim 5, wherein the co-crystal is present in a therapeutically effective amount.

12. The method of claim 11, wherein the virus is selected from the group consisting of: adenovirus, herpes simplex virus, human pepillomavrus, VITAMIN K virus, smallpox virus, hepatitis B virus (HBV), parvovirus B19, human astrovirus, norwalk virus, hepatitis A virus (HAV), severe acute respiratory syndrome virus, hepatitis C virus (HCV), yellow fever virus, dengue virus, West Nile virus, TBE virus, rubella virus, hepatitis E virus (HEV), human immunodeficiency virus (HIV), influenza virus, Lassa virus (LASV), Crimean-Congo hemorrhagic fever virus, Hantaan virus, Ebola virus, Marburg virus, Measles virus, mumps virus, parainfluenza virus, respiratory syncytial virus, rabies virus, hepatitis D virus (HDV), rotavirus, orbivirus, coltivirus, and Banna virus.

13. The method of claim 11, wherein the virus is hepatitis B virus (HBV), hepatitis C virus (HCV), human immunodeficiency virus (HIV) or Hantaan virus.

14. The method of claim 11, wherein the pharmaceutical composition is administered via infusion, injection or the oral route.

15. The method of claim 11, wherein the pharmaceutical composition is an aqueous composition comprising an effective amount of the co-crystal and pharmaceutically acceptable amount of at least one therapeutic agent or adjuvant dissolved or dispersed in a pharmaceutically acceptable carrier or aqueous media.

16. A process of producing the co-crystal of claim 1, comprising: (i) providing carboplatin and 1,2-cis-cyclobutane dicarboxylate at a ratio in a solvent; (ii) slurrying or stirring the mixtures for a period of time; and (iii) isolating the co-crystal formed in step (ii).

17. The process of claim 16, wherein the ratio of carboplatin to 1,2-cis-cyclobutane dicarboxylate is about 1:11 in molar.

* * * * *